(12) United States Patent
Hayden et al.

(10) Patent No.: US 12,357,624 B2
(45) Date of Patent: Jul. 15, 2025

(54) LOW DOSE PRIDOPIDINE FOR PARKINSON'S DISEASE AND OTHER DISEASES ASSOCIATED WITH PARKINSONISM

(71) Applicant: PRILENIA NEUROTHERAPEUTICS LTD., Herzliya (IL)

(72) Inventors: Michael Hayden, Herzliya (IL); Michal Geva, Even-Yehuda (IL); Angela Cenci Nilsson, Lund (SE)

(73) Assignee: Prilenia Neurotherapeutics Ltd., Yakum (IL)

( * ) Notice: Subject to any disclaimer, the term of this patent is extended or adjusted under 35 U.S.C. 154(b) by 1016 days.

(21) Appl. No.: 17/425,951

(22) PCT Filed: Feb. 4, 2020

(86) PCT No.: PCT/IL2020/050134
§ 371 (c)(1),
(2) Date: Jul. 27, 2021

(87) PCT Pub. No.: WO2020/161707
PCT Pub. Date: Aug. 13, 2020

(65) Prior Publication Data
US 2022/0193059 A1   Jun. 23, 2022

Related U.S. Application Data

(60) Provisional application No. 62/800,803, filed on Feb. 4, 2019.

(51) Int. Cl.
*A61K 31/451* (2006.01)
*A61P 25/16* (2006.01)

(52) U.S. Cl.
CPC ............ *A61K 31/451* (2013.01); *A61P 25/16* (2018.01)

(58) Field of Classification Search
CPC .............................. A61K 31/451; A61P 25/16
See application file for complete search history.

(56) References Cited

U.S. PATENT DOCUMENTS

| | | | |
|---|---|---|---|
| 6,903,120 | B2 | 6/2005 | Sonesson |
| 7,417,043 | B2 | 8/2008 | Sonesson |
| 7,923,459 | B2 | 4/2011 | Gauthier et al. |
| 9,006,445 | B2 | 4/2015 | Sonesson et al. |
| 9,012,476 | B2 | 4/2015 | Zimmermann et al. |
| 9,139,525 | B2 | 9/2015 | Wikström |
| RE46,117 | E | 8/2016 | Sonesson et al. |
| 9,796,673 | B2 | 10/2017 | Wu et al. |
| 9,814,706 | B2 | 11/2017 | Zimmermann et al. |
| 10,047,049 | B2 | 8/2018 | Barel et al. |
| 10,130,621 | B2 | 11/2018 | Schmidt |
| 10,322,119 | B2 | 6/2019 | Bassan |
| 10,406,145 | B2 | 9/2019 | Schmidt |
| 10,603,311 | B2 | 3/2020 | Geva |
| 2013/0197031 | A1 | 8/2013 | Sonesson |
| 2013/0267552 | A1 | 10/2013 | Waters |
| 2015/0202302 | A1 | 7/2015 | Licht |
| 2016/0095847 | A1 | 4/2016 | Sonesson |
| 2016/0166559 | A1 | 6/2016 | Sonesson |
| 2017/0020854 | A1 | 1/2017 | Licht |
| 2017/0266170 | A1 | 9/2017 | Waters |
| 2018/0055832 | A1 | 3/2018 | Hayden |
| 2018/0235950 | A1 | 8/2018 | Sonesson |
| 2019/0015401 | A1 | 1/2019 | Sonesson |
| 2019/0046516 | A1 | 2/2019 | Russ |
| 2019/0192496 | A1 | 6/2019 | Borowsky |
| 2019/0209542 | A1 | 7/2019 | Bassan |
| 2019/0231768 | A1 | 8/2019 | Geva |
| 2019/0336488 | A1 | 11/2019 | Hayden |
| 2019/0350914 | A1 | 11/2019 | Geva |
| 2019/0350915 | A1 | 11/2019 | Bassan |
| 2020/0000785 | A1 | 1/2020 | Waters et al. |
| 2020/0030308 | A1 | 1/2020 | Schmidt et al. |

FOREIGN PATENT DOCUMENTS

| | | |
|---|---|---|
| WO | WO 2001/046145 | 6/2001 |
| WO | WO 2006/040155 | 4/2006 |
| WO | WO 2008/127188 | 10/2008 |
| WO | WO 2012/002863 | 3/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138130 | 9/2016 |
| WO | WO 2016/138135 | 9/2016 |
| WO | WO 2017/015609 | 1/2017 |
| WO | WO 2017/015615 | 1/2017 |
| WO | WO 2017/147366 | 8/2017 |

(Continued)

OTHER PUBLICATIONS

Jia et al. Frontiers in Cellular Neuroscience, Sep. 2018, Volumn 12, Article 314.*
Mollenhauer et al. Science, Aug. 19, 2022, vol. 377, Issue 6608, pp. 818-819.*
Aaseth et al., Biometals (2018) 31: 737-747.*
Mitsui, Jun, "Glucocerebrosidase involvement in Parkinson disease", History of Medicine (Igaku no Ayumi), Special Edition (Bessatsu), 2014(10), pp. 105-107, Ishiyaku Pub. Inc.
Bae, E. J. et al. (2014). Glucocerebrosidase depletion enhances cell-to-cell transmission of α-synuclein. Nature communications, 5(1), 1-11.
Blume, S. R. et al. (2009). Stepping test in mice: a reliable approach in determining forelimb akinesia in MPTP-induced Parkinsonism. Experimental neurology, 219(1), 208-211.

(Continued)

*Primary Examiner* — Rebecca L Anderson
(74) *Attorney, Agent, or Firm* — Mark S. Cohen; PEARL COHEN ZEDEK LATZER BARATZ LLP

(57) ABSTRACT

The subject invention provides a method for treating Parkinsonism or symptoms thereof by low dose pridopidine.

21 Claims, 21 Drawing Sheets

(56) References Cited

FOREIGN PATENT DOCUMENTS

| WO | WO 2018/039475 | 3/2018 |
|---|---|---|
| WO | WO 2018/039477 | 3/2018 |
| WO | WO 2018/053275 | 3/2018 |
| WO | WO 2018/053280 | 3/2018 |
| WO | WO 2018/053287 | 3/2018 |
| WO | WO 2018/136600 | 7/2018 |
| WO | WO 2019/036358 | 2/2019 |
| WO | WO 2019/046568 | 3/2019 |
| WO | WO 2019/050775 | 3/2019 |

OTHER PUBLICATIONS

Chang, J. W. et al. (1999). Biochemical and anatomical characterization of forepaw adjusting steps in rat models of Parkinson's disease: studies on medial forebrain bundle and striatal lesions. Neuroscience, 88(2), 617-628.

Christ, M. G. et al. (2019). Sigma-1 receptor activation induces autophagy and increases proteostasis capacity in vitro and in vivo. Cells, 8(3), 211.

Cicchetti, F. et al. (2002). Neuroinflammation of the nigrostriatal pathway during progressive 6-OHDA dopamine degeneration in rats monitored by immunohistochemistry and PET imaging. European Journal of Neuroscience, 15(6), 991-998.

Cousins, M. S. et al. (1996). Skilled motor deficits in rats induced by ventrolateral striatal dopamine depletions: behavioral and pharmacological characterization. Brain research, 732(1-2), 186-194.

De Yebenes, J. G. et al. & MermaiHD study investigators. (2011). Pridopidine for the treatment of motor function in patients with Huntington's disease (MermaiHD): a phase 3, randomised, double-blind, placebo-controlled trial. The Lancet Neurology, 10(12), 1049-1057.

Eddings, C. R. et al. (2019). Pridopidine protects neurons from mutant-huntingtin toxicity via the sigma-1 receptor. Neurobiology of disease, 129, 118-129.

Fernandes, H. J. et al. (2016). ER stress and autophagic perturbations lead to elevated extracellular α-synuclein in GBA-N370S Parkinson's IPSC-derived dopamine neurons. Stem cell reports, 6(3), 342-356.

Francardo, V. et al. (2011). Impact of the lesion procedure on the profiles of motor impairment and molecular responsiveness to L-DOPA in the 6-hydroxydopamine mouse model of Parkinson's disease. Neurobiology of disease, 42(3), 327-340.

Francardo, V. et al. (2014). Pharmacological stimulation of sigma-1 receptors has neurorestorative effects in experimental parkinsonism. Brain, 137(7), 1998-2014.

Francardo, V. et al. (2019). Pridopidine induces functional neurorestoration via the sigma-1 receptor in a mouse model of Parkinson's disease. Neurotherapeutics, 16(2), 465-479.

Fujimoto, M. et al. (2012). Sigma-1 receptor chaperones regulate the secretion of brain-derived neurotrophic factor. Synapse, 66(7), 630-639.

Garcia-Martinez, J. M. et al. (2006). Glial cell line-derived neurotrophic factor promotes the arborization of cultured striatal neurons through the p42/p44 mitogen-activated protein kinase pathway. Journal of neuroscience research, 83(1), 68-79.

Garcia-Miralles, M. et al. (2017). Early pridopidine treatment improves behavioral and transcriptional deficits in YAC128 Huntington disease mice. JCI insight, 2(23).

Geva, M. et al. (2016). Pridopidine activates neuroprotective pathways impaired in Huntington Disease. Human molecular genetics, 25(18), 3975-3987.

Granado, N. et al. (2018). Striatal reinnervation process after acute methamphetamine-induced dopaminergic degeneration in mice. Neurotoxicity research, 34(3), 627-639.

Greene, T. W. et al. (1999). Protective groups in organic synthesis—3rd edition—John Wiley & Sons.

Hayashi, T. et al. (2007). Sigma-1 receptor chaperones at the ER-mitochondrion interface regulate Ca2+ signaling and cell survival. Cell, 131(3), 596-610.

Huntington Study Group HART Investigators. (2013). A randomized, double-blind, placebo-controlled trial of pridopidine in Huntington's disease. Movement Disorders, 28(10), 1407-1415.

International Search Report for PCT Application No. PCT/IL2020/050134 dated Apr. 26, 2020.

Ionescu, A. et al. (2019). Targeting the sigma-1 receptor via pridopidine ameliorates central features of ALS pathology in a SOD1 G93A model. Cell death & disease, 10(3), 1-19.

Johnston, T. H. et al. (2018). Pridopidine, a clinic-ready compound, reduces 3, 4-dihydroxyphenylalanine-induced dyskinesia in Parkinsonian macaques. Movement Disorders, 34(5), 708-716.

Kusko, R. et al. (2018). Large-scale transcriptomic analysis reveals that pridopidine reverses aberrant gene expression and activates neuroprotective pathways in the YAC128 HD mouse. Molecular neurodegeneration, 13(1), 1-15.

Li, H. et al. (2019). Mitochondrial dysfunction and mitophagy defect triggered by heterozygous GBA mutations. Autophagy, 15(1), 113-130.

Lundblad, M. et al. (2002). Pharmacological validation of behavioural measures of akinesia and dyskinesia in a rat model of Parkinson's disease. European Journal of Neuroscience, 15(1), 120-132.

Magalhaes, J. et al. (2016). Autophagic lysosome reformation dysfunction in glucocerebrosidase deficient cells: relevance to Parkinson disease. Human molecular genetics, 25(16), 3432-3445.

March, J. (1992). Advanced Organic Chemistry Reaction, Mechanisms, And Structure.4th Ed., pp. 351-357—John Wiley and Sons.

McGarry, A. et al. (2017). Safety and exploratory efficacy at 36 months in Open-HART, an open-label extension study of pridopidine in Huntington's disease. Journal of Huntington's disease, 6(3), 189-199.

Menzies, F. M. et al. (2015). Compromised autophagy and neurodegenerative diseases. Nature Reviews Neuroscience, 16(6), 345-357.

Mysona, B. A. et al. (2018). Relationship between Sigma-1 receptor and BDNF in the visual system. Experimental eye research, 167, 25-30.

Nguyen, L. et al. (2015). Role of sigma-1 receptors in neurodegenerative diseases. Journal of pharmacological sciences, 127(1), 17-29.

Nurnberger, L. et al. (2017). Late-Breaking Abstracts, MDS Study Group Abstracts and Guided Poster Tour Information, International Congress of Parkinson's Disease and Movement Disorders, Retrieved from: https://www.mdscongress.org/Congress-2017-Files/PDF/LBASGGPT.pdf, Retrieved on: Mar. 10, 2017 Jun. 8, 2017 (Jun. 8, 2017) slides 49-50.

Penas, C. et al. (2011). Sigma receptor agonist 2-(4-morpholinethyl) 1 phenylcyclohexanecarboxylate (Pre084) increases GDNF and BiP expression and promotes neuroprotection after root avulsion injury. Journal of neurotrauma, 28(5), 831-840.

Perry, V. H. et al. (Sep. 2013). Microglia and macrophages of the central nervous system: the contribution of microglia priming and systemic inflammation to chronic neurodegeneration. In Seminars in immunopathology (vol. 35, No. 5, pp. 601-612). Springer Berlin Heidelberg.

Rabinovich-Guilatt, L. et al. (2016). The effect of mild and moderate renal impairment on the pharmacokinetics of pridopidine, a new drug for Huntington's disease. British journal of clinical pharmacology, 81(2), 246-255.

Rabinovich-Guilatt, L. et al. (2017). Metoprolol-pridopidine drug-drug interaction and food effect assessments of pridopidine, a new drug for treatment of Huntington's disease. British journal of clinical pharmacology, 83(10), 2214-2224.

Reilmann, R. et al. & European Huntington's Disease Network. (2019). Safety and efficacy of pridopidine in patients with Huntington's disease (PRIDE-HD): a phase 2, randomised, placebo-controlled, multicentre, dose-ranging study. The Lancet Neurology, 18(2), 165-176.

Ryskamp, D. et al. (2017). The sigma-1 receptor mediates the beneficial effects of pridopidine in a mouse model of Huntington disease. Neurobiology of disease, 97, 46-59.

(56) References Cited

OTHER PUBLICATIONS

Ryskamp, D. et al. (2019). Pridopidine stabilizes mushroom spines in mouse models of Alzheimer's disease by acting on the sigma-1 receptor. Neurobiology of disease, 124, 489-504.
Sahlholm, K. et al. (2013). The dopamine stabilizers ACR16 and (-)-OSU6162 display nanomolar affinities at the σ-1 receptor. Molecular psychiatry, 18(1), 12-14.
Sahlholm, K. et al. (2015). Pridopidine selectively occupies sigma-1 rather than dopamine D2 receptors at behaviorally active doses. Psychopharmacology, 232(18), 3443-3453.
Sanchez-Martinez, A. et al. (2016). Parkinson disease-linked GBA mutation effects reversed by molecular chaperones in human cell and fly models. Scientific reports, 6(1), 1-12.
Schapira, A. H. (2015). Glucocerebrosidase and Parkinson disease: recent advances. Molecular and Cellular Neuroscience, 66, 37-42.
Smith-Dijak, A. I. et al. (2019). Impairment and restoration of homeostatic plasticity in cultured cortical neurons from a mouse model of huntington disease. Frontiers in cellular neuroscience, 13, 209.
Song, D. D. et al. (2000). Striatal responses to partial dopaminergic lesion: evidence for compensatory sprouting. Journal of Neuroscience, 20(13), 5102-5114.
Vairo, F. et al. (2015). Brain-derived neurotrophic factor expression increases after enzyme replacement therapy in Gaucher disease. Journal of neuroimmunology, 278, 190-193.
West, M. J. (1999). Stereological methods for estimating the total number of neurons and synapses: issues of precision and bias. Trends in neurosciences, 22(2), 51-61.
Westin, J. E. et al. (2006). Endothelial proliferation and increased blood-brain barrier permeability in the basal ganglia in a rat model of 3, 4-dihydroxyphenyl-L-alanine-induced dyskinesia. Journal of Neuroscience, 26(37), 9448-9461.
Winkler, C. et al. (1999). Intranigral transplants of GABA-rich striatal tissue induce behavioral recovery in the rat Parkinson model and promote the effects obtained by intrastriatal dopaminergic transplants. Experimental neurology, 155(2), 165-186.
Xie, W. et al. (2012). Alpha-synuclein impairs normal dynamics of mitochondria in cell and animal models of Parkinson's disease. Journal of neurochemistry, 122(2), 404-414.
Yang, H. et al. (2019). SIGMAR1/Sigma-1 receptor ablation impairs autophagosome clearance. Autophagy, 15(9), 1539-1557.
Agosta, F., et al. (2013). White matter abnormalities in Parkinson's disease patients with glucocerebrosidase gene mutations. Movement Disorders, 28(6), 772-778.
Bandres-Ciga, S., et al. (2020). Genetics of Parkinson's disease: an introspection of its journey towards precision medicine. Neurobiology of disease, 137, 104782.
Brockmann, K., et al. (2011). GBA-associated PD presents with nonmotor characteristics. Neurology, 77(3), 276-280.
Cilia, R., et al. (2016). Survival and dementia in GBA-associated Parkinson's disease: The mutation matters. Annals of neurology, 80(5), 662-673.
Cisbani, G., et al. (2012). An in vitro perspective on the molecular mechanisms underlying mutant huntingtin protein toxicity. *Cell death & disease*, 3(8), e382-e382.
Filippi, M., et al. (2022). Neuroimaging in glucocerebrosidase-associated Parkinsonism: A systematic review. Movement Disorders, 37(7), 1375-1393.
Leocadi, M., et al. (2022). Longitudinal clinical, cognitive, and neuroanatomical changes over 5 years in GBA-positive Parkinson's disease patients. Journal of Neurology, 1-16.
Lythe, V., et al. (2017). GBA-associated Parkinson's disease: progression in a deep brain stimulation cohort. Journal of Parkinson's disease, 7(4), 635-644.
Sezgin, M., et al. (2021). Functional connectivity analysis in heterozygous glucocerebrosidase mutation carriers. Journal of Parkinson's Disease, 11(2), 559-568.
Skrahin, A., et al. (2024). GBA1-Associated Parkinson's Disease Is a Distinct Entity. International Journal of Molecular Sciences, 25(13), 7102.

\* cited by examiner

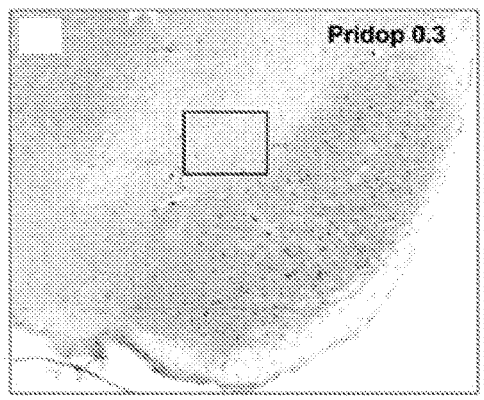
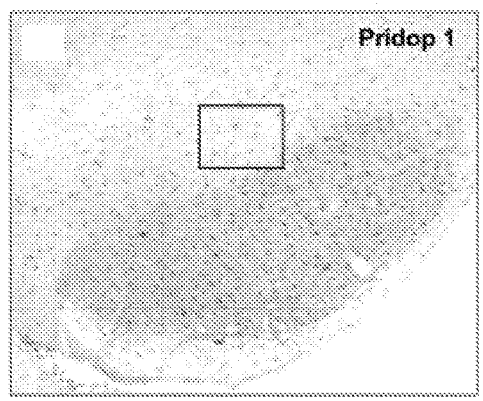
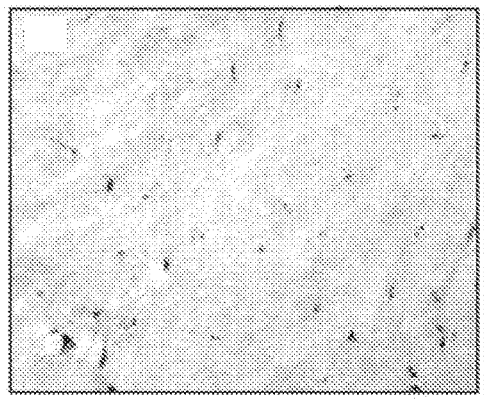
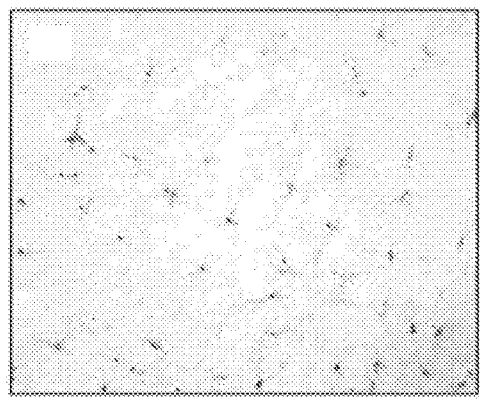
Figure 3C
Figure 3D
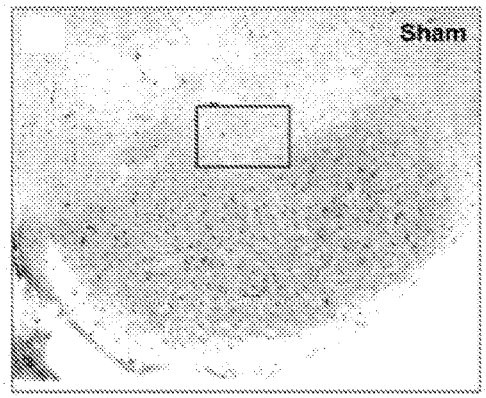
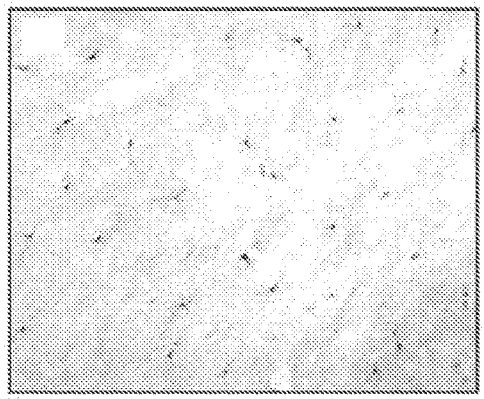
Figure 3E

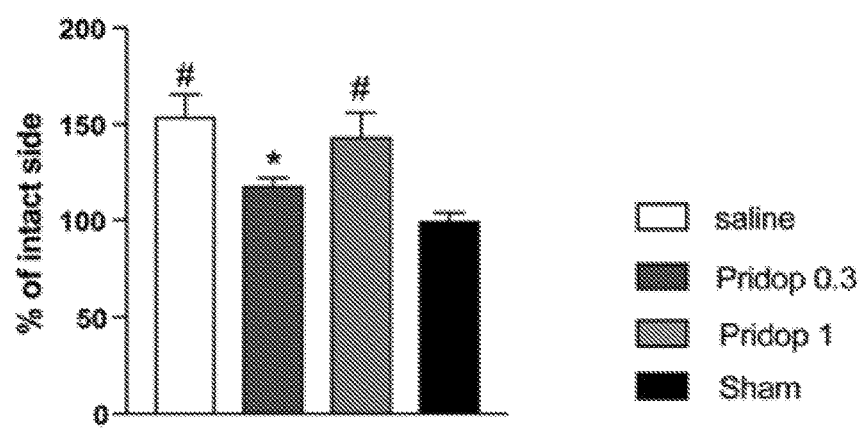
Figure 3F
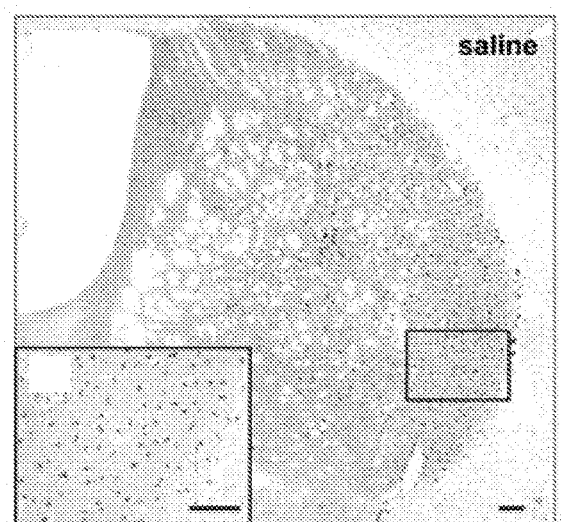 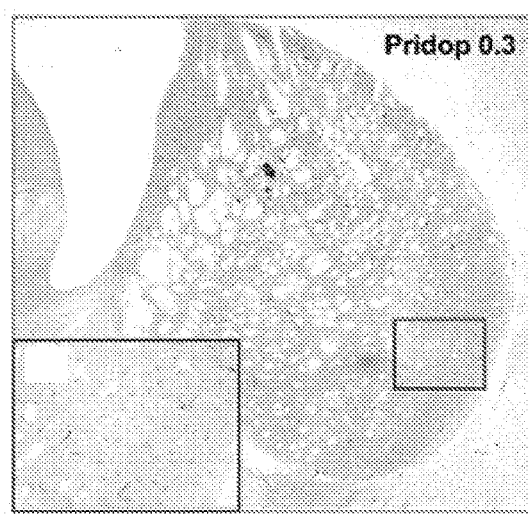
Figure 3G  Figure 3H

Figure 3I                                         Figure 3J

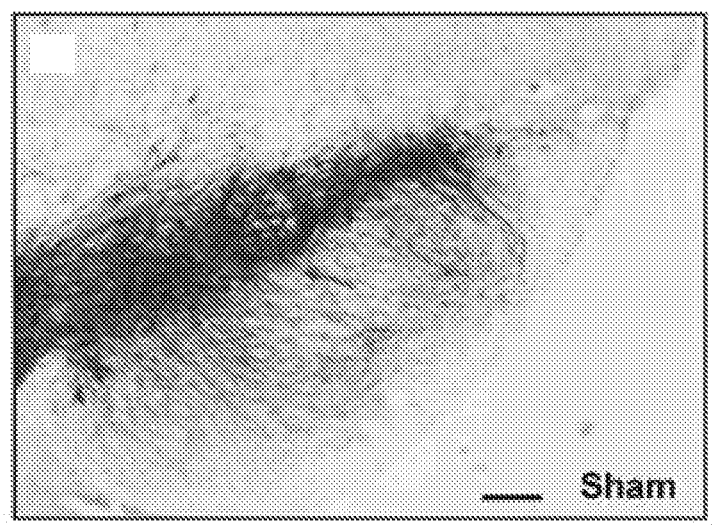
Figure 5D
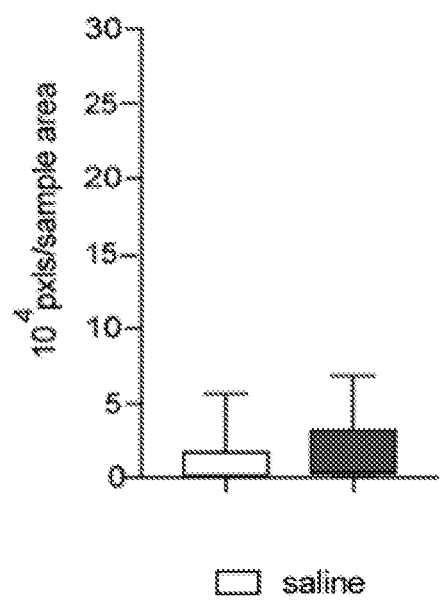
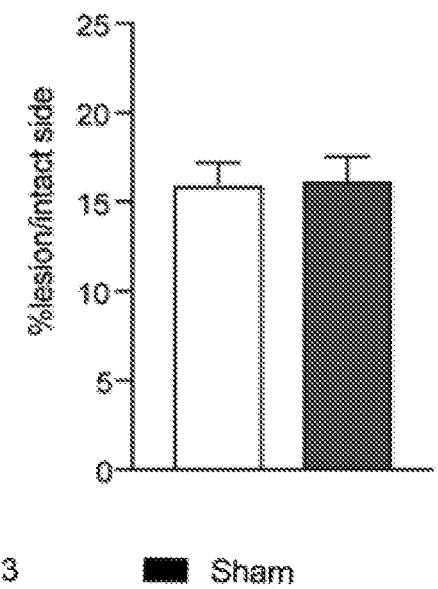
Figure 5E
Figure 5F

LOW DOSE PRIDOPIDINE FOR PARKINSON'S DISEASE AND OTHER DISEASES ASSOCIATED WITH PARKINSONISM

FIELD OF THE INVENTION

The subject invention provides a method for treating a subject afflicted with Parkinson's Disease or parkinsonism associated with other diseases, comprising administering to the subject low dose of pridopidine or pharmaceutically acceptable salt thereof.

BACKGROUND OF THE INVENTION

Pridopidine (4-[3-(methylsulfonyl)phenyl]-1-propyl-piperidine) (formerly known as ACR16) has been found to improve motor function in Huntington disease (HD) patients and animal models of HD. Although its motor effects were originally attributed its low affinity antagonism on dopamine receptors, in vivo PET studies in rats show that behaviorally relevant doses of pridopidine occupy the Sigma-1 receptor (S1R) rather than the dopamine D2/D3Rs. This is in-line with in-vitro binding affinity assays showing a much higher binding affinity at the S1R compared to the D2R (Ki for S1R~100 nM, Ki for D2R 10-30 µM and Ki for D3R 1.6 uM). The S1R is a ligand-operated chaperone protein, enriched at mitochondria-associated endoplasmic reticulum membranes (MAMs), supporting several pathways of cell defense and survival. S1R modulates multiple cellular mechanisms, including up-regulation of anti-apoptotic genes, reduced microglial activation, reduced generation of reactive oxygen species (ROS) and nitric oxide (NO), and an increased secretion of trophic factors.

Parkinson's disease (PD) is an age-related neurodegenerative disease where reciprocal interactions between alpha-synuclein aggregation, oxidative stress, mitochondrial dysfunction, and neuroinflammation play a central pathogenic role.

SUMMARY OF THE INVENTION

The present invention provides, in one aspect, method for preventing, treating, or slowing the progression of Parkinson's Disease or another disease associated with Parkinson's Disease or another disease associated with parkinsonism or symptom thereof in a subject in need thereof, comprising administering to the subject at least one pharmaceutical composition per day, wherein the pharmaceutical composition comprises pridopidine or pharmaceutically acceptable salt thereof, and wherein the total administered dosage of the pridopidine or pharmaceutically acceptable salt thereof is 1 to 100 mg per day.

In certain embodiments, the method comprises preventing, treating, slowing, or reversing functional decline of the subject.

In certain embodiments, the functional decline of the subject is presented as a symptom selected from the group consisting of tremor, bradykinesia, rigidity, postural instability, a decline according to the Unified Parkinson's Disease Rating Scale part II (UPDRS part II), including Activities of Daily living, and a decline according to the Modified Hoehn and Yahr Staging of PD.

In certain embodiments, the method comprises preventing, treating, slowing, or reversing cognitive decline of the subject.

In certain embodiments, the cognitive decline of the subject is presented as a symptom selected from the group consisting of intellectual impairment, thought disorder, depression, decreased motivation, decreased initiative, impaired speech, increased salvation, impaired swallowing, impaired handwriting, and increased pain sensation.

In certain embodiments, the method comprises preventing, treating, slowing, or reversing neurodegeneration in the subject.

In certain embodiments, the neurodegeneration in the subject is presented as decreased fibroblast GCase activity, increased ER stress, neuronal mitochondrial dysfunction, increased neuronal mitochondrial ROS production, decreased autophagic flux, decreased neuronal mitochondria velocity, decreased mitophagy, decreased plasma BDNF levels, decreased cerebrospinal fluid (CSF) BDNF levels, decreased neuronal and BDNF axonal transport, increased protein aggregates in the brain or cerebrospinal fluid (CSF), brain inflammation, increased microglial activation, increased astrocyte activation, decreased brain volume, increased neurofilament light (NFL) plasma levels, or increased neurofilament light (NFL) cerebrospinal fluid (CSF) levels.

In certain embodiments, the method comprises administering to the subject a pharmaceutical composition comprising pridopidine or pharmaceutically acceptable salt thereof at least twice a day.

In certain embodiments, the method comprises administering to the subject a pharmaceutical composition comprising pridopidine or pharmaceutically acceptable salt thereof twice a day.

In certain embodiments, the method comprises administering to the subject a pharmaceutical composition comprising pridopidine or pharmaceutically acceptable salt thereof three times a day.

In certain embodiments, the method comprises administering to the subject a pharmaceutical composition comprising pridopidine or pharmaceutically acceptable salt thereof four times a day.

In certain embodiments, the total administered dosage of the pridopidine or pharmaceutically acceptable salt thereof is 10 to 100 mg per day.

In certain embodiments, the total administered dosage of the pridopidine or pharmaceutically acceptable salt thereof is 50 to 100 mg per day.

In certain embodiments, the total administered dosage of the pridopidine or pharmaceutically acceptable salt thereof is 80 to 100 mg per day.

In certain embodiments, the total administered dosage of the pridopidine or pharmaceutically acceptable salt thereof is 80 mg per day.

In certain embodiments, the total administered dosage of the pridopidine or pharmaceutically acceptable salt thereof is 90 mg per day.

In certain embodiments, the total administered dosage of the pridopidine or pharmaceutically acceptable salt thereof is 100 mg per day.

In certain embodiments, the method comprises administering to the subject a pharmaceutical composition comprising pridopidine or pharmaceutically acceptable salt thereof twice a day, wherein the total administered dosage of the pridopidine or pharmaceutically acceptable salt thereof is 80 to 100 mg per day.

In certain embodiments, the method comprises administering to the subject a pharmaceutical composition comprising pridopidine or pharmaceutically acceptable salt thereof twice a day, wherein the total administered dosage of the pridopidine or pharmaceutically acceptable salt thereof is 90 mg per day.

In certain embodiments, the method comprises administering to the subject a pharmaceutical composition comprising pridopidine or pharmaceutically acceptable salt thereof twice a day, wherein each one of the two pharmaceutical composition comprises a different dosage of pridopidine or pharmaceutically acceptable salt thereof, wherein the total administered dosage of the pridopidine or pharmaceutically acceptable salt thereof is 90 mg per day.

In certain embodiments, the method comprises administering to the subject a pharmaceutical composition comprising 45 mg pridopidine or pharmaceutically acceptable salt thereof twice a day, wherein the total administered dosage of the pridopidine or pharmaceutically acceptable salt thereof is 90 mg per day.

In certain embodiments, the method comprises systemically administering the pharmaceutical composition comprising pridopidine or pharmaceutically acceptable salt thereof to the subject.

In certain embodiments, the method comprises orally administering the pharmaceutical composition comprising pridopidine or pharmaceutically acceptable salt thereof to the subject.

In certain embodiments, the pharmaceutical composition comprising pridopidine or pharmaceutically acceptable salt thereof is administered in a form selected from the group consisting of an inhalable powder, an injectable, a liquid, a gel, a solid, a capsule or a tablet.

In certain embodiments, the pharmaceutically acceptable pridopidine salt is pridopidine hydrochloride.

In certain embodiments, the Parkinsonism or symptom thereof is part of, or associated with, a neurodegenerative condition selected from the group consisting of Parkinson's disease (PD), multiple system atrophy (MSA), dementia with Lewy bodies (DLB), amyotrophic lateral sclerosis (ALS), Parkinson's disease dementia (PDD), Huntington's disease (HD), Alzheimer's disease, progressive supranuclear palsy (PSP), corticobasal degeneration, Frontotemporal dementia, Gerstmann-Sträussler-Scheinker syndrome, Lytico-bodig disease (ALS complex of Guam), neuroacanthocytosis, neuronal ceroid lipofuscinosis, olivopontocerebellar atrophy, pantothenate kinase-associated neurodegeneration, Wilson's disease, corticobasal degeneration (CBD), and Pick's disease.

In certain embodiments, the Parkinsonism or symptom thereof is part of, or associated with, Parkinson's disease (PD).

In certain embodiments, the PD is associated with a glucocerebrosidase mutation (PD-GB A).

In certain embodiments, the Parkinsonism or symptom thereof is part of, or associated with, multiple system atrophy (MSA).

In certain embodiments, the Parkinsonism or symptom thereof is part of, or associated with, dementia with Lewy bodies (DLB).

In certain embodiments, the Parkinsonism or symptom thereof is part of, or associated with, amyotrophic lateral sclerosis (ALS).

In one embodiment this invention is directed to a method for treating Parkinson's disease (PD) in a subject in need thereof comprising administering to the subject low dose of pridopidine or pharmaceutically acceptable salt thereof, thereby treating the subject.

In one embodiment this invention is directed to a method of slowing the functional decline in a subject afflicted with PD, comprising administering to the subject low dose of pridopidine or pharmaceutically acceptable salt thereof, thereby slowing the functional decline in subject afflicted with PD.

In one embodiment this invention is directed to a method of inducing/promoting functional neurorestoration in a subject afflicted with PD, comprising administering to the subject a low dose of pridopidine or pharmaceutically acceptable salt thereof, thereby inducing/promoting functional neurorestoration in a subject afflicted with PD.

In another embodiment, the parkinsonism is associated with Parkinson's disease associated with glucocerebrosidase (GBA) deficiency (PD-GBA), Multiple System Atrophy (MSA) or Lewy Body Dementia (LBD).

In another embodiment, the pridopidine is pridopidine hydrochloride.

In another embodiment, the pridopidine is administered orally.

In another embodiment, the pridopidine is administered in the form of an inhalable powder, an injectable, a liquid, a gel, a solid, a capsule or a tablet.

In another embodiment, the pridopidine is administered periodically.

In another embodiment, the pridopidine is administered less often than once daily.

In another embodiment, the pridopidine is administered in one dose two doses or three doses per day.

In another embodiment, pridopidine is administered in a daily dose of between 10 mg/day-100 mg/day.

In another embodiment, pridopidine is administered in a daily dose of between 20 mg/day-90 mg/day.

In another embodiment, pridopidine is administered in a daily dose of between 45 mg/day-90 mg/day.

In another embodiment, pridopidine is administered in a daily dose of between 20 mg/day-50 mg/day

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 1A) spontaneous rotations: ANOVA $p<0.0001$ time, treatment, interaction; time $F(4,160)=50.46$, treatment $F(3,40)=16.97$, interaction $F(12,160)=5.43$; (FIG. 1B) cylinder test: ANOVA $p>0.05$ interaction; $<0.0001$ time and treatment; time F(4,160)=8.74, treatment F(3,40)=20.96, interaction F(12,160)=1.52; (FIG. 1C) stepping test: ANOVA p=0.006 interaction; p=0.0004 time, p<0.0001 treatment, time F(4,160)=5.46, treatment F(340)=75.44, interaction F(12,160)=2.44; p<0.05, asterisk, versus "saline"; number sign, versus "sham"; ampersand versus "Pridop 1".

(FIG. 2A) Stereological counts of TH-positive cells were performed in the substantia nigra pars compacta (SNc) (the dashed line outlines the area included in the analysis). Data show the total number of cells from the SNc ipsilateral to the lesion (mean±SEM from 7 sections per animal throughout the SNc). One-way ANOVA p<0.0001; F (3,39)=44.29; post hoc Tukey test, p<0.05 asterisk versus saline; number sign, versus sham. (FIGS. 2B-2E) Low-magnification photomicrographs of nigral sections immune-stained for TH, representing the different groups. Scale bar 100 µm. (FIGS. 2F-2K) Low-magnification photomicrographs of striatal sections; the dashed line represents the area included in the analysis of TH fiber density. (FIGS. 2F'-2H') High-magnification insets from the same sections illustrate differences in fiber density and morphology between the different groups (FIG. 2F', saline-treated case; FIG. 2G', mouse treated with 0.3 mg/kg pridopidine, FIG. 2H', mouse treated with 1 mg/kg pridopidine). Scale bar, 200 µm. (FIG. 2I) Image segmentation analysis of TH-positive fibers as performed at high magnification on random sample areas. Values give fiber pixels/sample area, whiskers encompass the entire range of values in each group (the median is shown as a horizontal line). Kruskal-Wallis and post hoc Dunn's test, p=0.0091; asterisk, p<0.05 versus saline. (FIGS. 2J-2K) Optical density analysis of TH immunostaining over the entire cross-sectional area of the ventrolateral (FIG. 2J) or dorsolateral (FIG. 2K) striatum; O.D. values from the side ipsilateral to the lesion are expressed as a percentage of those from the contralateral intact side in each animal (mean±SEM from 4 sections per animal throughout the striatum). (FIG. 2J) VL striatum, ANOVA p=0.0002, F (2,33)=11.35; (K) DL striatum, ANOVA p=0.039, F (2,33)=3.56. Post hoc Tukey test, p<0.05 asterisk, versus saline; ampersand, vs Pridop 1.

FIG. 4 Pridopidine low dose (0.3 mg/kg) does not improve motor deficits in 6-OHDA-lesioned mice that lack S1R. Spontaneous rotations (FIG. 4A) and forelimb use asymmetry (cylinder test, FIG. 4B, and stepping test, FIG. 4C) were assessed once a week in S1R KO mice sustaining 6-OHDA lesions or sham lesions, followed by treatment with either 0.3 mg/kg pridopidine (Pridop 0.3) or saline solution (n=8-10 per group). Results are expressed as number of spontaneous ipsilateral rotations during a 10-min test session (A) or as a percentage of supporting wall contacts (FIG. 4B) and adjusting steps (FIG. 4C) performed with the paw contralateral to the lesion (left paw). Repeated-measures ANOVA and post hoc Bonferroni test.

(FIG. 5 A) Stereological counts of TH-positive cells in the SNc in S1R KO mice and (FIG. 5B-5D) low-magnification photomicrographs of nigral sections immune-stained for TH (the dashed line outlines the area included in the analysis). Scale bar, 100 µm. Data in A show the total number of cells from the SNc ipsilateral to the lesion (mean±SEM from 7 sections per animal throughout the SNc). One-way ANOVA p<0.0001, F (2,26)=41.73; post hoc Bonferroni test; p<0.05 number sign versus sham group. (FIG. 5 E) Image segmentation analysis of TH-positive fibers as performed at high magnification on random sample areas through the lateral striatum (encased by dashed lines). Values are expressed as fiber pixels/sample area, whiskers encompass the entire range of values in each group, the median is shown as a bar. Mann-Whitney test, p=0.084. (FIG. 5F) Ventrolateral (VL) striatum, unpaired t test, p=0.516; (FIG. 5G) Dorsolateral (DL) striatum, p=0.219.

DETAILED DESCRIPTION OF THE INVENTION

Figure 1A:
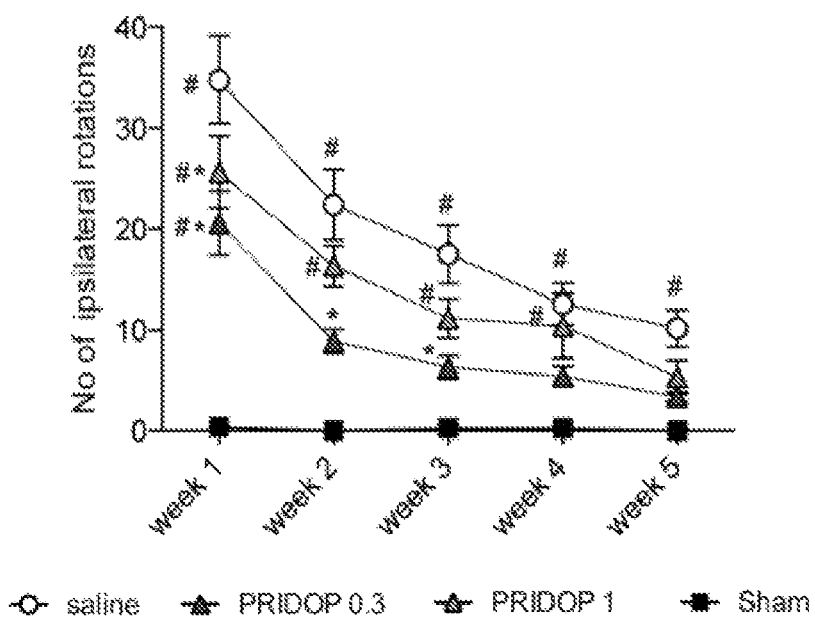
FIGS. 1A-1C show behavioral improvement upon treatment with low dose of pridopidine. Spontaneous rotations (FIG. 1A) and forelimb use asymmetry (cylinder test, B, and stepping test, C) were assessed once a week in mice treated with either 0.3 or 1 mg/kg pridopidine (Pridop 0.3 or Pridop 1 mg/kg, respectively) or saline solution (n=8-12 per group). Results are expressed as number of spontaneous ipsilateral rotations during a 10-min test session (FIG. 1A) or as a percentage of supporting wall contacts (FIG. 1B) and adjusting steps (FIG. 1C) performed with the paw contralateral to the lesion (left paw). The lower dose of pridopidine (0.3 mg/kg) improved the animals' performance in all the tests. The improvement in the forelimb use (FIGS. 1B and 1C) occurred gradually and became prominent after 5 weeks of treatment. Significant overall differences were found for the low dose, pridopidine 0.3 mg/kg treated mice, but not for the higher dose 1 mg/kg pridopidine treated mice, in all these tests using repeated-measures ANOVA and post hoc Bonferroni test.

The present invention provides, on an aspect, a method for preventing, treating, or slowing the progression of Parkinson's Disease or another disease associated with parkinsonism or symptom thereof in a subject in need thereof, comprising administering to the subject at least one pharmaceutical composition per day, wherein the pharmaceutical composition comprises pridopidine or pharmaceutically acceptable salt thereof, and wherein the total administered dosage of the pridopidine or pharmaceutically acceptable salt thereof is 1 to 100 mg per day.

In certain embodiments, the method is for preventing, treating, or slowing the progression of Parkinson's Disease. In certain embodiments, the method is for preventing, treating, or slowing the progression of a disease associated with parkinsonism. In certain embodiments, the method is for preventing, treating, or slowing the progression of a symptom of Parkinson's Disease. In certain embodiments, the method is for preventing, treating, or slowing the progression of a symptom of a disease associated with parkinsonism. In certain embodiments, the method is for preventing, treating, or slowing the progression of a symptom of associated with parkinsonism.

In certain embodiments, the method comprises preventing, treating, slowing, or reversing functional decline of the subject. In certain embodiments, the method comprises preventing functional decline of the subject. In certain embodiments, the method comprises treating functional decline of the subject. In certain embodiments, the method comprises slowing functional decline of the subject. In certain embodiments, the method comprises reversing functional decline of the subject.

In certain embodiments, the functional decline of the subject is presented as a symptom selected from the group consisting of tremor, bradykinesia, rigidity, postural instability, a decline according to the Unified Parkinson's Disease Rating Scale part II (UPDRS part II), including Activities of Daily living, and a decline according to the Modified Hoehn and Yahr Staging of PD. In certain embodiments, the functional decline of the subject is presented as tremor. In certain embodiments, the functional decline of the subject is presented as bradykinesia. In certain embodiments, the functional decline of the subject is presented as rigidity. In certain embodiments, the functional decline of the subject is presented as postural instability. In certain embodiments, the functional decline of the subject is presented as a decline according to the Unified Parkinson's Disease Rating Scale part II (UPDRS part II), including Activities of Daily living. In certain embodiments, the functional decline of the subject is presented as a decline according to the Modified Hoehn and Yahr Staging of PD.

In certain embodiments, the method comprises preventing, treating, slowing, or reversing cognitive decline of the subject. In certain embodiments, the method comprises preventing cognitive decline of the subject. In certain embodiments, the method comprises treating cognitive decline of the subject. In certain embodiments, the method comprises slowing cognitive decline of the subject. In certain embodiments, the method comprises reversing cognitive decline of the subject.

In certain embodiments, the cognitive decline of the subject is presented as a symptom selected from the group consisting of intellectual impairment, thought disorder, depression, decreased motivation, decreased initiative, impaired speech, increased salvation, impaired swallowing, impaired handwriting, and increased pain sensation. In certain embodiments, the cognitive decline of the subject is presented as intellectual impairment. In certain embodiments, the cognitive decline of the subject is presented as thought disorder. In certain embodiments, the cognitive decline of the subject is presented as depression. In certain embodiments, the cognitive decline of the subject is presented as decreased motivation. In certain embodiments, the cognitive decline of the subject is presented as decreased initiative. In certain embodiments, the cognitive decline of the subject is presented as impaired speech. In certain embodiments, the cognitive decline of the subject is presented as increased salvation. In certain embodiments, the cognitive decline of the subject is presented as impaired swallowing. In certain embodiments, the cognitive decline of the subject is presented impaired handwriting. In certain embodiments, the cognitive decline of the subject is presented as increased pain sensation.

In certain embodiments, the method comprises preventing, treating, slowing, or reversing neurodegeneration in the subject. In certain embodiments, the method comprises preventing neurodegeneration in the subject. In certain embodiments, the method comprises treating neurodegeneration in the subject. In certain embodiments, the method comprises slowing neurodegeneration in the subject. In certain embodiments, the method comprises reversing neurodegeneration in the subject.

In certain embodiments, the neurodegeneration in the subject is presented as decreased fibroblast GCase activity, increased ER stress, neuronal mitochondrial dysfunction, increased neuronal mitochondrial ROS production, decreased autophagic flux, decreased neuronal mitochondria velocity, decreased mitophagy, decreased plasma BDNF levels, decreased cerebrospinal fluid (CSF) BDNF levels, decreased neuronal and BDNF axonal transport, increased protein aggregates in the brain or cerebrospinal fluid (CSF), brain inflammation, increased microglial activation, increased astrocyte activation, decreased brain volume, increased neurofilament light (NFL) plasma levels, or increased neurofilament light (NFL) cerebrospinal fluid (CSF) levels.

In certain embodiments, the neurodegeneration in the subject is presented as decreased fibroblast GCase activity. In certain embodiments, the neurodegeneration in the subject is presented as increased ER stress. In certain embodiments, the neurodegeneration in the subject is presented as neuronal mitochondrial dysfunction. In certain embodiments, the neurodegeneration in the subject is presented as increased neuronal mitochondrial ROS production. In certain embodiments, the neurodegeneration in the subject is presented as decreased autophagic flux. In certain embodiments, the neurodegeneration in the subject is presented as decreased neuronal mitochondria velocity. In certain embodiments, the neurodegeneration in the subject is presented as decreased mitophagy. In certain embodiments, the neurodegeneration in the subject is presented as decreased plasma BDNF levels. In certain embodiments, the neurodegeneration in the subject is presented as decreased cerebrospinal fluid (CSF) BDNF levels. In certain embodiments, the neurodegeneration in the subject is presented as decreased neuronal and BDNF axonal transport. In certain embodiments, the neurodegeneration in the subject is presented as increased protein aggregates in the brain or cerebrospinal fluid (CSF). In certain embodiments, the neurodegeneration in the subject is presented as brain inflammation. In certain embodiments, the neurodegeneration in the subject is presented as increased microglial activation. In certain embodiments, the neurodegeneration in the subject is presented as increased astrocyte activation. In certain embodiments, the neurodegeneration in the subject is presented as decreased brain volume. In certain embodiments, the neurodegeneration in the subject is presented as increased neurofilament light (NFL) plasma levels. In certain embodiments, the neurodegeneration in the subject is presented as increased neurofilament light (NFL) cerebrospinal fluid (CSF) levels.

In certain embodiments, the method comprises administering to the subject a pharmaceutical composition comprising pridopidine or pharmaceutically acceptable salt thereof at least twice a day. In certain embodiments, the method comprises administering to the subject a pharmaceutical composition comprising pridopidine or pharmaceutically acceptable salt thereof at least three times a day. In certain embodiments, the method comprises administering to the subject a pharmaceutical composition comprising pridopidine or pharmaceutically acceptable salt thereof at least four times a day.

In certain embodiments, the method comprises administering to the subject a pharmaceutical composition comprising pridopidine or pharmaceutically acceptable salt thereof twice a day.

In certain embodiments, the method comprises administering to the subject a pharmaceutical composition comprising pridopidine or pharmaceutically acceptable salt thereof three times a day.

In certain embodiments, the method comprises administering to the subject a pharmaceutical composition comprising pridopidine or pharmaceutically acceptable salt thereof four times a day.

In certain embodiments, the total administered dosage of the pridopidine or pharmaceutically acceptable salt thereof is 10 to 100 mg per day. In certain embodiments, the total administered dosage of the pridopidine or pharmaceutically acceptable salt thereof is 20 to 100 mg per day. In certain embodiments, the total administered dosage of the pridopidine or pharmaceutically acceptable salt thereof is 30 to 100 mg per day. In certain embodiments, the total administered dosage of the pridopidine or pharmaceutically acceptable salt thereof is 40 to 100 mg per day. In certain embodiments, the total administered dosage of the pridopidine or pharmaceutically acceptable salt thereof is 50 to 100 mg per day. In certain embodiments, the total administered dosage of the pridopidine or pharmaceutically acceptable salt thereof is 60 to 100 mg per day. In certain embodiments, the total administered dosage of the pridopidine or pharmaceutically acceptable salt thereof is 70 to 100 mg per day. In certain embodiments, the total administered dosage of the pridopidine or pharmaceutically acceptable salt thereof is 80 to 100 mg per day. In certain embodiments, the total administered dosage of the pridopidine or pharmaceutically acceptable salt thereof is 90 to 100 mg per day.

In certain embodiments, the total administered dosage of the pridopidine or pharmaceutically acceptable salt thereof is 80 mg per day. In certain embodiments, the total administered dosage of the pridopidine or pharmaceutically acceptable salt thereof is 85 mg per day. In certain embodiments, the total administered dosage of the pridopidine or pharmaceutically acceptable salt thereof is 90 mg per day. In certain embodiments, the total administered dosage of the pridopidine or pharmaceutically acceptable salt thereof is 95 mg per day. In certain embodiments, the total administered dosage of the pridopidine or pharmaceutically acceptable salt thereof is 100 mg per day.

In certain embodiments, the method comprises administering to the subject a pharmaceutical composition comprising pridopidine or pharmaceutically acceptable salt thereof twice a day, wherein the total administered dosage of the pridopidine or pharmaceutically acceptable salt thereof is 80 to 100 mg per day. In certain embodiments, the method comprises administering to the subject a pharmaceutical composition comprising pridopidine or pharmaceutically acceptable salt thereof twice a day, wherein the total administered dosage of the pridopidine or pharmaceutically acceptable salt thereof is 85 to 95 mg per day.

In certain embodiments, the method comprises administering to the subject a pharmaceutical composition comprising pridopidine or pharmaceutically acceptable salt thereof twice a day, wherein the total administered dosage of the pridopidine or pharmaceutically acceptable salt thereof is 90 mg per day.

In certain embodiments, the method comprises administering to the subject a pharmaceutical composition comprising pridopidine or pharmaceutically acceptable salt thereof twice a day, wherein each one of the two pharmaceutical composition comprises a different dosage of pridopidine or pharmaceutically acceptable salt thereof, wherein the total administered dosage of the pridopidine or pharmaceutically acceptable salt thereof is 90 mg per day.

In certain embodiments, the method comprises administering to the subject a pharmaceutical composition comprising 45 mg pridopidine or pharmaceutically acceptable salt thereof twice a day, wherein the total administered dosage of the pridopidine or pharmaceutically acceptable salt thereof is 90 mg per day.

In certain embodiments, the method comprises systemically administering the pharmaceutical composition comprising pridopidine or pharmaceutically acceptable salt thereof to the subject.

In certain embodiments, the method comprises orally administering the pharmaceutical composition comprising pridopidine or pharmaceutically acceptable salt thereof to the subject.

In certain embodiments, the pharmaceutical composition comprising pridopidine or pharmaceutically acceptable salt thereof is administered in a form selected from the group consisting of an inhalable powder, an injectable, a liquid, a gel, a solid, a capsule or a tablet. In certain embodiments, the pharmaceutical composition comprising pridopidine or pharmaceutically acceptable salt thereof is administered in a form of powder. In certain embodiments, the pharmaceutical composition comprising pridopidine or pharmaceutically acceptable salt thereof is administered in a form of an injectable material. In certain embodiments, the pharmaceutical composition comprising pridopidine or pharmaceutically acceptable salt thereof is administered in a form of a liquid. In certain embodiments, the pharmaceutical composition comprising pridopidine or pharmaceutically acceptable salt thereof is administered in a form of a gel. In certain embodiments, the pharmaceutical composition comprising pridopidine or pharmaceutically acceptable salt thereof is administered in a form of a solid. In certain embodiments, the pharmaceutical composition comprising pridopidine or pharmaceutically acceptable salt thereof is administered in a form of a capsule. In certain embodiments, the pharmaceutical composition comprising pridopidine or pharmaceutically acceptable salt thereof is administered in a form of a tablet.

In certain embodiments, the pharmaceutically acceptable pridopidine salt is pridopidine hydrochloride.

In certain embodiments, the Parkinsonism or symptom thereof is part of, or associated with, a neurodegenerative condition selected from the group consisting of Parkinson's disease (PD), multiple system atrophy (MSA), dementia with Lewy bodies (DLB), amyotrophic lateral sclerosis (ALS), Parkinson's disease dementia (PDD), Huntington's disease (HD), Alzheimer's disease (AD), progressive supranuclear palsy (PSP), corticobasal degeneration, Frontotemporal dementia, Gerstmann-Sträussler-Scheinker syndrome, Lytico-bodig disease (ALS complex of Guam), neuroacanthocytosis, neuronal ceroid lipofuscinosis, olivopontocerebellar atrophy, pantothenate kinase-associated neurodegeneration, Wilson's disease, corticobasal degeneration (CBD), and Pick's disease.

In certain embodiments, the Parkinsonism or symptom thereof is part of, or associated with, PD. In certain embodiments, the Parkinsonism or symptom thereof is part of, or associated with, MSA. In certain embodiments, the Parkinsonism or symptom thereof is part of, or associated with, DLB. In certain embodiments, the Parkinsonism or symptom thereof is part of, or associated with, ALS. In certain embodiments, the Parkinsonism or symptom thereof is part of, or associated with, PDD. In certain embodiments, the Parkinsonism or symptom thereof is part of, or associated with, HD. In certain embodiments, the Parkinsonism or symptom thereof is part of, or associated with, AD. In certain embodiments, the Parkinsonism or symptom thereof is part of, or associated with, PSP. In certain embodiments, the Parkinsonism or symptom thereof is part of, or associated with, corticobasal degeneration. In certain embodiments, the Parkinsonism or symptom thereof is part of, or associated with, Frontotemporal dementia. In certain embodiments, the Parkinsonism or symptom thereof is part of, or associated with, Gerstmann-Sträussler-Scheinker syndrome. In certain embodiments, the Parkinsonism or symptom thereof is part of, or associated with, Lytico-bodig disease. In certain embodiments, the Parkinsonism or symptom thereof is part of, or associated with, neuroacanthocytosis. In certain embodiments, the Parkinsonism or symptom thereof is part of, or associated with, neuronal ceroid lipofuscinosis. In certain embodiments, the Parkinsonism or symptom thereof is part of, or associated with, olivopontocerebellar atrophy. In certain embodiments, the Parkinsonism or symptom thereof is part of, or associated with, pantothenate kinase-associated neurodegeneration. In certain embodiments, the Parkinsonism or symptom thereof is part of, or associated with, Wilson's disease. In certain embodiments, the Parkinsonism or symptom thereof is part of, or associated with, CBD. In certain embodiments, the Parkinsonism or symptom thereof is part of, or associated with, Pick's disease.

In certain embodiments, the Parkinsonism or a symptom thereof is part of, or associated with, Parkinson's disease (PD). In certain embodiments, the PD is PD-GBA.

In certain embodiments, the Parkinsonism or a symptom thereof is part of, or associated with, multiple system atrophy (MSA).

In certain embodiments, the Parkinsonism or a symptom thereof is part of, or associated with, dementia with Lewy bodies (DLB).

In certain embodiments, the Parkinsonism or a symptom thereof is part of, or associated with, amyotrophic lateral sclerosis (ALS).

This invention further provides a method for treating, inhibiting or reducing the decline of PD in a subject in need thereof comprising administering to the subject low dose of pridopidine or pharmaceutically acceptable salt thereof, thereby treating the subject.

This invention further provides a method of slowing functional decline in a subject afflicted with PD, comprising administering to the subject low dose of pridopidine or pharmaceutically acceptable salt thereof, thereby slowing the functional decline in a in a subject afflicted with PD.

This invention further provides a method of inducing/promoting functional neurorestoration in a subject afflicted with PD, comprising administering to the subject a low dose of pridopidine or pharmaceutically acceptable salt thereof, thereby inducing/promoting functional neurorestoration in in a subject afflicted with PD.

In another embodiment, this invention further provides a method of treating Parkinson's Disease (PD) associated with glucocerebrosidase (GBA) mutations, GBA deficiency, Multiple System Atrophy (MSA) or Lewy Body Dementia (LBD). In another embodiment, this invention further provides a method of treating PD associated with GBA mutation. In another embodiment, this invention further provides a method of treating PD associated with GBA deficiency. In another embodiment, this invention further provides a method of treating parkinsonism associated with Multiple System Atrophy (MSA). In another embodiment, this invention further provides a method of treating parkinsonism associated with Lewy Body Dementia (LBD).

Mutations in the GBA gene, which encodes the lysosomal hydrolase glucocerebrosidase (GCase) are the most common risk factor for developing Parkinson's Disease (PD), and between 5 and 20% of PD patients are carriers. PD-GBA patients have a younger age of onset, and more associated cognitive changes than the general PD patient population.

There is a clinical link between PD and the lysosomal storage disorder Gaucher Disease (GD), which is caused by a recessive mutation in the GBA gene. GD patients and gene carriers are at increased risk for developing PD. Several cellular mechanisms are proposed to contribute to GBA-associated neurodegeneration, including (1) ER stress, (2) mitochondrial dysfunction, (3) defects in autophagy, and (4) defects in BDNF levels and axonal transport.

Parkinsonism is an early feature of both MSA and LBD. MSA symptoms include motor impairments (loss of or limited muscle control or movement, or limited mobility) may include tremor, rigidity, and/or loss of muscle coordination as well as difficulties with speech and gait (the way a person walks) similar to PD.

MSA is a rare disease, including men and women and all racial groups. Symptoms tend to appear in a person's 50s and advance rapidly over the course of 5 to 10 years, with progressive loss of motor function and eventual confinement to bed. currently there are no drugs that are able to slow disease progression and there is no cure. MSA includes disorders that historically had been referred to as Shy-Drager syndrome, olivopontocerebellar atrophy, and striatonigral degeneration.

Lewy Body Dementia (LBD) is a progressive brain disorder in which Lewy bodies (abnormal deposits of a protein called alpha-synuclein) build up in areas of the brain that regulate behavior, cognition, and movement similar to PD.

In one embodiment, the subject is a human patient.

In one embodiment, the pridopidine is administered orally. In one embodiment, the pridopidine is administered orally.

In one embodiment, the pridopidine is administered in the form of an inhalable powder, an injectable, a liquid, a gel, a solid, a capsule or a tablet.

In one embodiment, the pridopidine is administered periodically.

In one embodiment, the pridopidine is administered less often than once daily. In one embodiment, the pridopidine is administered daily. In one embodiment, the pridopidine is administered once daily. In another embodiment, the pridopidine is administered more often than once daily. In one embodiment, the pridopidine is administered twice daily or three times a day.

In one embodiment, the amount of pridopidine administered in low dose of between 10 mg/day and 100 mg/day. In one embodiment, the amount of pridopidine administered is between 20 mg/day-90 mg/day. In one embodiment, the amount of pridopidine administered is 45 mg/day-90 mg/day. In one embodiment, the amount of pridopidine administered is 20 mg/day-50 mg/day. In another embodiment, the amount of pridopidine administered is about 20 mg/day, 22.5 mg/day, about 45 mg/day, about 67.5 mg/day, about 90 mg/day, about 100 mg/day. In an embodiment, the amount of pridopidine administered is 45 mg/day. In an embodiment, the amount of pridopidine administered is 90 mg/day.

In one embodiment, the amount of pridopidine is administered in one dose per day. In one embodiment, the amount of pridopidine is administered in two doses per day.

In one embodiment, the amount of pridopidine administered in a dose is about 10 mg, about 22.5 mg, about 45 mg, about 67.5 mg, about 90 mg.

In one embodiment, the amount of pridopidine is administered in two doses per day at an amount of 45 mg per dose.

In one embodiment, the periodic administration of pridopidine continues for at least 3 days, at least 30 days, at least 42 days, at least 8 weeks, at least 12 weeks, at least 24 weeks, at least 6 months, at least 1 year, at least 2 years, at least 5 years, at least 10 years, at least 15 years, at least 20 years, at least 25 years, or 30 years or more.

In one embodiment, the pridopidine treats the subject by delaying the onset of symptoms in the subject.

For the foregoing embodiments, each embodiment disclosed herein is contemplated as being applicable to each of the other disclosed embodiments. In addition, the elements recited in method embodiments can be used in the pharmaceutical composition, use, and package embodiments described herein and vice versa.

Terms

As used herein, and unless stated otherwise, each of the following terms shall have the definition set forth below.

As used herein, "pridopidine" means pridopidine base or a pharmaceutically acceptable salt thereof.

The active compound for use according to the invention may be provided in any form suitable for the intended administration. Suitable forms include pharmaceutically acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of acid addition salts of the compound of the present invention include, but is not limited to, the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. In certain embodiments, pridopidine is a pharmaceutically acceptable salt, such as the HCl salt or tartrate salt. Preferably, in any embodiments of the invention as described herein, the pridopidine is in the form of its hydrochloride salt.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would be greater than 90 mg due to the presence of the salt.

As a person in the field would understand, the terms "increased" or "decreased", when referring to any type of symptom of a patient, is in comparison to the presence and/or severity of he symptom in a corresponding healthy subject, to a corresponding group of healthy subjects, or to the history of the patient itself.

The term "functional decline" refers in some embodiments to one or more of a subject's capabilities of maintaining occupation, taking care of finances, domestic chores, requiring low level of care and activities of daily living (ADL). In some embodiments, the methods of this invention provides a method of preventing, treating, slowing, or reversing of the subject capabilities of one or more of maintaining occupation, taking care of finances, domestic chores, requiring low level of care and activities of daily living (ADL).

An additional functional impairment/disability assessment is incorporated in the UDysRS scale for patients with dyskinesia. This scale invites direct observation of the patient's ability to carry out ADLs. Parts 3 and 4 of the UDysRS address how the patient's ADL functionality is impacted.

The term "functional decline" includes, e.g. in the case of PD patients, a decline according to the Unified Parkinson's Disease Rating Scale part II (UPDRS part II), including Activities of Daily living. For example, the Modified Hoehn and Yahr Staging of PD includes: Stage 0 (no signs of disease), Stage 1 (unilateral disease), Stage 1.5 (unilateral plus axial involvement), Stage 2 (bilateral disease, without impairment of balance), Stage 2.5 (mild bilateral disease, with recovery on pull test), Stage 3 (mild to moderate bilateral disease; some postural instability; physically independent), Stage 4 (severe disability; still able to walk or stand unassisted), and Stage 5 (wheelchair bound or bedridden unless aided).

The term "Activities of Daily living" further includes a decline according to the Schwab and England Activities of Daily Living Scale, which includes: 100% (Completely independent. Able to do all chores without slowness, difficulty or impairment. Essentially normal. Unaware of any difficulty.), 90% (Completely independent. Able to do all chores with some degree of slowness, difficulty and impairment. Might take twice as long. Beginning to be aware of difficulty.), 80% (Completely independent in most chores. Takes twice as long. Conscious of difficulty and slowness.), 70% (Not completely independent. More difficulty with some chores. Three to four times as long in some. Must spend a large part of the day with chores.), 60% (Some dependency. Can do most chores, but exceedingly slowly and with much effort. Errors; some impossible.), 50% (More dependent. Help with half, slower, etc. Difficulty with everything.), 40% (Very dependent. Can assist with all chores, but few alone.), 30% (With effort, now and then does a few chores alone or begins alone. Much help needed.), 20% (Nothing alone. Can be a slight help with some chores. Severe invalid.), 10% (Totally dependent, helpless. Complete invalid.), and 0% (Vegetative functions such as swallowing, bladder and bowel functions are not functioning. Bedridden.).

As used herein, a "unit dose", "unit doses" and "unit dosage form(s)" mean a single drug administration entity/entities. A "unit dose", "unit doses" and "unit dosage form(s)" can be prepared for oral dosage forms, such as tablets, capsules, pills, powders, and granules.

As used herein, "about" in the context of a numerical value or range means 90-110% of the numerical value or range recited or claimed.

"Administering to the subject" or "administering to the (human) patient" means the giving of, dispensing of, or application of medicines, drugs, or remedies to a subject/patient to delay, relieve, cure, or reduce the symptoms associated with a condition, e.g., a pathological condition. Oral administration is one way of administering the instant compounds to the subject.

A compound according to the subject invention may be administered in the base form or in the form of pharmaceutically acceptable salts, preferably in a pharmaceutical composition together with one or more adjuvants, excipients, carriers, buffers, diluents, and/or other customary pharmaceutical auxiliaries.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compound to the subject.

The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

"Treat" or "treating" as used herein encompasses alleviating, lessening, reducing the severity of, eliminating or substantially eliminating, or ameliorating a physical, mental or emotional limitation in a subject afflicted with PD. Treating also refers to delaying or prevention of symptoms or reduction of deficits associated with a disease.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of PD. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

It is understood that where a parameter range is provided, all integers within that range, and tenths thereof, are also provided by the invention. For example, "22 mg-300.0 mg" includes 22.0 mg, 22.1 mg, 22.2 mg, 22.3 mg, 22.4 mg, etc. up to 300.0 mg inclusive.

This invention will be better understood by reference to the Experimental Details which follow, but those skilled in the art will readily appreciate that the specific Examples are only illustrative of the invention as described more fully in the claims which follow thereafter.

EXAMPLES

The effects of pridopidine as a potential S1R agonist in hemi-parkinsonian rodents was studied. Mice with intrastriatal 6-hydroxydopamine (6-OHDA) lesions were treated with pridopidine for 5 weeks. The results show surprisingly that at low dose (such as 0.3 mg/kg), pridopidine produces behavioral and neurohistological restoration, accompanied by upregulation of neuroplasticity pathways in the striatum. Pridopidine treatment did not show any of these beneficial effects in 6-OHDA-lesioned mice lacking S1R. Pharmacokinetic data show that at the effective dosage (0.3 mg/kg), pridopidine maximum brain concentration (Cmax) is 110 ng/ml, a concentration sufficient to selectively bind the S1R, but not the dopamine receptors. These results are the first to demonstrate that, by acting like a S1R agonist, pridopidine can protect degenerating dopamine neuron and reinstate functionally significant levels of dopaminergic fibers in the motor striatum.

Methods:

Animals

The study was performed in male C57B16J mice weighing approx. 25 g and having an age of 8 to 9 weeks at the beginning of the experiments. A total of 65 wild-type mice and 52 S1R knockout (KO) mice were used. S1R knockout mice and wild-type littermates (both genders) were bred on a C57BL6J background. Our S1R KO line is derived from the well-characterized Sigmar1$^{Gt(OST422756)Lex}$ mouse strain distributed by the Mutant Mouse Resource Regional Centre (MMRRC) The mice were housed under a 12-h light/dark cycle with free access to food and water. Housing conditions and experimental treatments had been approved by the Malmo-Lund Ethical Committee on Animal Research.

6-OHDA Lesions

Lesions were performed according to previously described procedures [Francardo V, Bez F, Wieloch T, Nissbrandt H, Ruscher K, Cenci 33. MA. Pharmacological stimulation of sigma-1 receptors has neurorestorative effects in experimental Parkinson's disease and parkinsonism. Brain: A Journal of Neurology. 2014; 137(Pt 7):1998-2014]. Briefly, mice were anesthetized with isofluorane (Isoba®vet, Apoteksbolaget, Solna, Stockholm, 108 Sweden) and placed in a stereotaxic frame on a flat-skull position. 6-OHDA-HCl (Sigma-Aldrich AB, Stockholm, Sweden) was freshly dissolved in 0.02% ascorbate-saline at the concentration of 3.2 mg free base per milliliter. One microliter of toxin solution per site was injected into the right striatum at the following coordinates (given in mm relative to the bregma, sagittal suture, and dural surface, cf. Paxinos and Franklin, 2001): AP+1.0, ML−2.1, and DV−2.9, site 1, and AP+0.3, ML−2.3, and DV−2.9, site 2. The solution was injected via a glass capillary (tip diameter−50 (1 m) at the rate of 0.5 (1 L/min, and the capillary was left in place for 2 mi after each injection.

Treatments

Pridopidine was dissolved in physiological saline immediately before use and injected at the volume of 0.1 mL/10 g body weight in a single subcutaneous (s.c.) injection per day. The first injection was given immediately upon completion of lesion surgery. In the first experiment, pridopidine was administered at either 0.3 or 1.0 mg/kg. After establishing that only 0.3 mg/kg pridopidine produced a functionally relevant neuro-restoration, this dose was selected for the rest of the study. Pridopidine was always administered at about 2 p.m., while behavioral tests were always performed in the morning between 9:00 and 10:30 a.m. (this time lag was allowed in order to rule out confounders due to potential motor effects of pridopidine).

Behavioral Tests

All the mice participating in this study underwent 3 behavioral tests once a week.

i) Spontaneous Rotational Activity

Postural and locomotor asymmetries resulting from unilateral nigrostriatal denervation were assessed using a test of spontaneous rotation in an open field. In this test, animals transiently turn towards the side ipsilateral to the 6-OHDA lesion in response to the novelty of the test environment, and the turning response gradually declines in all animals upon test repetition [Francardo V, Bez F, Wieloch T, Nissbrandt H, Ruscher K, Cenci 33. MA. Impact of the lesion procedure on the profiles of motor impairment and molecular responsiveness to L-DOPA in the 6-hydroxydopamine mouse model of Parkinson's disease. Neurobiology of Disease. 2011; 42(3): 327-340].

Briefly, each mouse was placed individually in the center of the open field (50×50 cm) and immediately video-recorded for 10 min, corresponding to the period of maximal activity [Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3): 327-340]. Full rotations (continuous turns of 360) were counted off-line by an experimentally blinded investigator. Data are expressed as the total number of net full turns ipsilateral to the lesion per test session.

ii) Cylinder Test

Forelimb use asymmetry during vertical exploration provides a validated measure of forelimb akinesia in hemiparkinsonian rodents [Lundblad M, Andersson M, Winkler C, Kirik D, Wierup N, Cenci M A. Pharmacological validation of behavioural measures of akinesia and dyskinesia in a rat model of Parkinson's disease. The European Journal of Neuroscience. 2002; 15(1):120-321. The test was executed as in [Francardo V, Bez F, Wieloch T, Nissbrandt H, Ruscher K, Cenci 33. MA. Briefly, mice were placed individually in a glass cylinder 161(10 cm diameter, 14 cm height) and videorecorded for 3 to 5 min. The number of supporting wall contacts performed independently by the paw contralateral to the lesion was expressed as a percentage of all supporting wall contacts in each session.

iii) Stepping Test

An impaired capacity to perform adjusting steps during experimenter-imposed movements (stepping test) reflects both akinetic and postural deficits relevant to PD [Blume S R, Cass D K, Tseng K Y. Stepping test in mice: a reliable approach in determining forelimb akinesia in MPTP-induced Parkinson's Disease. Experimental Neurology. 2009; 219(1):208-11. Winkler C, Bentlage C, Nikkhah G, Samii M, Bjorklund A. Intranigral transplants of GABA-rich striatal tissue induce behavioral recovery in the rat Parkinson's Disease model and promote the effects obtained by intrastriatal dopaminergic transplants. Experimental Neurology. 1999; 155(2):165-86]. The mouse was placed at the entrance of a custom-made plastic corridor (7 cm wide, 1 m long, flanked by 10-cm-high walls), gently lifted by the tail, and pulled backwards with a fixed speed (1 m/4 s). Each trial was video-recorded, and the footage was used to count the number of adjusting steps performed by each forelimb. Trials in which mice turned their body by 90° towards the walls of the corridor (in an attempt to escape or explore) were discarded. In each session, mice were tested until 3 valid trials per animal were obtained. Results were expressed as the percentage of steps performed by the forelimb contralateral to the lesion (left) over the total number of steps (mean of 3 trials per session).

Brain Preparation

Mice allocated to immunohistochemistry were perfusion-fixed on the day after the last rug/saline administration (interval of approx. 20 h from the last injection). Animals were deeply anesthetized with sodium pentobarbital (240 mg/kg, i.p.) and transcardially perfused with 0.9% saline solution, followed by ice-cold buffered 4% paraformaldehyde (pH 7.4). After rapid extraction, brains were immersed in the same fixative for 2 h and then cryoprotected in ice-cold phosphate-buffered 25% sucrose solution overnight. Coronal sections of 30 (1 m thickness were cut on a sliding microtome and stored at −20° C. in a nonfreezing solution (30% ethylene glycol and 30% glycerol in 0.1 M phosphate buffer).

Animals prepared for Western blot analysis were euthanized by cervical dislocation; their brains were rapidly extracted and frozen on crushed dry ice. Tissue samples were dissected out in a cryostat chamber (−14° C.). A coronal brain slice spanning across rostrocaudal levels, +1.18 to −0.34 mm relative to the bregma was extracted using a mouse brain shape container. The striatum was dissected out using a scalpel blade. Tissue samples from the substantia nigra were taken with a tissue puncher of 2 mm diameter spanning across rostrocaudal levels −2.70 to −3.80 relative to the bregma. The samples were kept frozen until further analysis.

Quantitative Immunohistochemistry

Immunohistochemistry and quantitative analyses were performed according to established protocols [Francardo V, Bez F, Wieloch T, Nissbrandt H, Ruscher K, Cenci 33. MA. Neurobiology of Disease. 2011; 42(3):327-340] using primary antibodies against tyrosine hydroxylase [Mysona B A, Zhao J, Smith S, Bollinger K E. Relationship between sigma-1 receptor and BDNF in the visual system. Experimental Eye Research. 2018; 167:25-30] (rabbit anti-TH antiserum from Pel-Freez, Rogers, AR, 1:1000) and Cluster of Differentiation 68 (CD68) (rat anti-CD68 antiserum from AbD Serotec, Kidlington, Oxfordshire, UK; 1:1000). Quantitative analyses were performed by an experimentally blinded investigator using the following methods.

The number of TH-positive cell bodies in the substantia nigra compacta (SNc) was determined using unbiased stereology according to the optical fractionator method as in [West M J. Stereological methods for estimating the total number of neurons and synapses: issues of precision and bias. Trends in Neurosciences. 1999; 22(2):51-61].

Analysis was performed using a Nikon 80i microscope with an x-y motorized stage controlled by the NewCAST software (Visiopharm). The sampling fraction was chosen so as to count at least 100 neurons per side per animal following an established protocol [Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3):327-340], and the total number of TH-positive neurons in the SNc was then estimated using the optical fractionator formula, i.e., number of neurons=1/ssf (slice sampling fraction)×1/asf (area sampling fraction)×1/tsf (thickness sampling fraction)×E (number of objects counted) [West M J. Stereological methods for estimating the total number of neurons and synapses: issues of precision and bias. Trends in Neurosciences. 1999; 22(2):51-61].

The density of TH-immunoreactive fibers was measured in the highly denervated lateral part of the striatum using an image segmentation software (VIS, Visiopharm Integrator System; Visiopharm, H0rsholm, DenmarK). To this end, the lateral striatum was outlined at low magnification (×4 objective) in a Nikon Eclipse 80i microscope, using well-defined anatomical landmarks, in 4 rostrocaudal levels per animal (as in [Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3):327-340]). An automatic random sampling was then applied under a ×100 objective to cover a fixed percentage of the structure of interest in all sections (10% of the lateral striatal cross-sectional area). Images were captured with a digital camera (Olympus DP72), obtaining 25 to 30 sample areas per mouse (area size, 5742 ($im^2$). On each image, distinct TH-immunopositive fibers were separated from background objects using a Bayesian algorithm-based pixel classifier [Westin J E, Lindgren H S, Gardi J, Nyengaard J R, Brundin P, Mohapel P, et al. Endothelial proliferation and increased blood-brain barrier permeability in the basal ganglia in a rat model of 3, 4-dihydroxyphenyl-L-alanine-induced dyskinesia. The Journal of Neuroscience: The Official Journal of the Society for Neuroscience. 2006; 26(37):9448-61].

Results were expressed as the total number of TH-immunopositive pixels per sample area (averaged across areas). This analysis was not carried out in the sham-lesioned animals because of the fine dopaminergic fiber mesh present in this group (type I fibers, [Song D D, Haber S N. Striatal responses to partial dopaminergic lesion: evidence for compensatory sprouting. The Journal of Neuroscience: The Official Journal of the Society for Neuroscience. 2000; 20(13):5102-14]), which precluded resolving distinct axonal structures. The high-magnification analysis of TH fibers on random sample areas was complemented by optical density (O.D.) measurements of TH immunostaining across the entire dorsolateral and ventro-lateral striatum. Although this method is much less sensitive than the actual fiber analysis [Francardo V, Bez F, Wieloch T, Nissbrandt H, Ruscher K, Cenci 33. MA. Pharmacological stimulation of sigma-1 receptors has neurorestorative effects in experimental parkinsonism. Brain: A Journal of Neurology. 2014; 137(Pt 7):1998-2014], it provides an indication of overall innervation density across the entire region of interest.

The O.D. analysis was carried out in the same rostrocaudal levels using *NIH Image J Software*, as described in [Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3):327-340]. After subtracting background values (measured in the corpus callosum in each animal), the O.D. on the side ipsilateral to the lesion was expressed as a percentage of that on the intact side in the same animal (values from the intact side representing normal innervation densities [Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3):327-340].

CD68-immunopositive cells exhibiting the morphology of active microglia [Cicchetti F, Brownell A L, Williams K, Chen Y I, Livni E, Isacson O. Neuroinflammation of the nigrostriatal pathway during progressive 6-OHDA dopamine degeneration in rats monitored by immunohistochemistry and PET imaging. The European Journal of Neuroscience. 2002; 15(6):991-8; Perry V H, Teeling J. Microglia and macrophages of the central nervous system: the contribution of microglia priming and systemic inflammation to chronic neurodegeneration. Seminars in Immunopathology. 2013; 35(5):601-12] were manually counted in the main body of the SNc (corresponding to rostrocaudal levels 3.40 to 3.64 posterior to the bregma) and ventrolateral striatum (0.26-0.02 anterior to the bregma). To this end, a mask delineating the region of interest was defined at ×4 magnification, and sample areas (36,921 (1 m$^2$ in size) were randomly picked within this mask under a ×40 objective using an x-y motorized stage controlled by the NewCAST software (Visiopharm). The number of CD68-immunopositive cells on the side ipsilateral to the lesion was expressed as a percentage of that on the contralateral side.

Western Blot Analysis

Tissue homogenates were prepared in cell lysis buffer (20 mmol/LTris (pH 7.5), 150 mmol/L NaCl, 1 mmol/L EDTA, 1 mmol/L EGTA, 1% Triton X-100, 2.5 mmol/L sodium pyrophosphate, 1 mmol/L |3-glycerolphosphate, 1 mmol/L Na3VO4, 11 g/mL leupeptin, and 1 mmol/L phenylmethylsulfonyl fluoride). Twenty micrograms of protein was separated on a 10% SDS polyacrylamide gel. Proteins were transferred onto polyvinyldifluoride membranes, which were incubated in blocking buffer (20 mM Tris, 136 mM NaCl, pH 7.6, 0.1% Tween 20, 5% nonfat dry milk). Thereafter, membranes were incubated overnight at 4° C. using one of the following primary antibodies: rabbit polyclonal anti-GDNF (Santa Cruz Biotechnology, Inc., Santa Cruz, CA; 1:1000) and monoclonal anti-BDNF (Santa Cruz Biotechnology, Inc., 1:1000); rabbit polyclonal antibodies against Thr202/Tyr204-phosphorylated ERK1/2 (p44/42-MAPK; Cell Signaling Technology Inc., Danvers, MA, 1:2000). Following appropriate washing steps, membranes were incubated with HRP-linked secondary antibodies (Sigma-Aldrich, Deisenhofen, Germany; 1:15000). Signals were visualized using a chemiluminescence kit (Merck Millipore, Watford, Hertfordshire, UK), and images were acquired using a CCD camera (LAS1000 system, Fuji Films, Tokyo, Japan). Optical density was measured on specific immunoreactive bands using NIH Image J software. Membranes were then stripped and reprobed with |-actin antibodies (Sigma-Aldrich, 1:50,000). The optical density of specific bands was then normalized to the |-actin band in the same lane.

Pridopidine Brain Tissue Binding

Brain binding characteristics of pridopidine were evaluated in vitro using fresh mouse brain homogenates by rapid equilibrium dialysis using rapid equilibrium dialysis (RED) Device Inserts from ThermoScientific, according to the manufacturer's protocol.

Statistical Analysis

Behavioral data recorded over the chronic treatment period were compared using repeated-measures analysis of variance (ANOVA) and post hoc Bonferroni test. All remaining analyses were performed using either unpaired t test or 1-factor ANOVA and post hoc Tukey test. Striatal fiber densities were analyzed using nonparametric statistics (Kruskal-Wallis and post hoc Dunn's test) because these data were not normally distributed. Unless otherwise stated, data are expressed as group mean±standard error of the mean (SEM). The exact p and F values of the ANOVAs are reported in the figure legends, whereas post hoc pairwise comparisons are reported as being either significant or nonsignificant. In all comparisons, the level of statistical significance is set at $p<0.05$.

ER Stress Measurement

ER stress levels can be measured using H2a-GFP as protein indicator of early stages of ER stress. H2a-GFP is a misfolded secretory protein which in response to ER stress accumulates. The STHdhQ7/7 is a striatal derived cell line from a knock in transgenic mouse containing homozygous humanized Huntingtin gene (HTT) with 7 polyglutamine repeats (wild type). STHdhQ7/7 cells are transfected with either Htt96Q-mCherry (mutant, mimics the typical pathogenic expression of Htt in HD patients) or Htt20Q-mCherry (normal) constructs. When the polyQ-expanded Htt protein (96Q) exon1 fused to fluorescent mCherry protein is expressed, the levels and aggregation of the protein in individual cells can be monitored using a fluorescent microscope.

Mitochondrial Dysfunction Induction and Measurement

Cortico-striatal neurons from YAC128 HD mice were treated with 1 μM pridopidine, and then stimulated with Antimycin A (Ant A, a piscicide inhibiting cellular respiration, specifically oxidative phosphorylation and ATP production) to induce mitochondrial Reactive Oxygen Species (ROS) production. Mitochondrial function was assayed by measuring the levels of the fluorescent probe MitoPY1, which detects $H_2O_2$ levels in mitochondria. Mitochondrial membrane potential (MMP) was assessed in cortical and striatal neurons using the positively changed fluorescent probe TMRM (tetramethylrhodamine methyl ester). Neurons were incubated with 150 nM TMRM (quenching conditions) in Na medium for 30 min at 37° C. Under these conditions, retention of TMRM by mitochondria was studied to estimate changes in $Dy_m$. Basal fluorescence (503 nm excitation and 525 nm emission) was recorded using a microplate reader Spectrofluorometer Gemini EM (Molecular Devices, USA) for 4 minutes, followed by the addition of 2.5 μM FCCP with 2.5 μg/mL oligomycin to produce maximal mitochondrial depolarization and mitochondrial probe release. TMRM release was calculated based in the differences in fluorescence before and after addition of oligomycin/FCCP.

Visualization and Analysis of Axonal Transport

In order to visualize and analyze axonal transport (AT), spinal cord extracts from WT or SOD1G93A embryos were plated in the proximal compartment of a microfluidic chamber. Retrograde axonal transport of Qdot-BDNF particles that were introduced exclusively to axons in the distal compartment were tracked using live imaging.

Example 1: Pridopidine Induces Behavioral Recovery in 6-OHDA-Lesioned Mice

Wild-type mice sustaining intrastriatal 6-OHDA lesions or sham lesions were treated daily with pridopidine (0.3 or 1.0 mg/kg) or vehicle solution ("saline") for 35 days starting on the same day of the lesion. In the final statistical analysis, sham-lesioned animals treated with pridopidine or saline were pooled in 1 group ("sham") after ascertaining that they had yielded quite similar results. A comparison of spontaneous turning behavior between groups and testing sessions revealed significant overall differences between treatments and time points (FIG. 1A). All groups injected with 6-OHDA exhibited a significant ipsilateral rotational bias, which was most pronounced on the first week and then gradually declined in all groups, as typically occurs with this test [Francardo V, Bez F, Wieloch T, Nissbrandt H, Ruscher K, Cenci 33. MA. Pharmacological stimulation of sigma-1 receptors has neurorestorative effects in experimental parkinsonism. Brain: A Journal of Neurology. 2014; 137(Pt 7):1998-2014; Francardo V, Recchia A, Popovic N, Andersson D, Nissbrandt H, Cenci M A. Impact of the lesion procedure on the profiles of motor impairment and molecular responsiveness to L-DOPA in the 6-hydroxydopamine mouse model of Parkinson's disease. Neurobiology of Disease. 2011; 42(3):327-340]. There were, however, highly significant differences between groups in the extent of this decline ($p < 0.0001$ for the interaction between treatment and time, see FIG. 1A). Indeed, 6-OHDA-lesioned mice treated with saline maintained a significant difference from sham-lesioned animals from the first through the fifth and last week, whereas mice treated with pridopidine no longer differed from sham-lesioned controls by the end of the treatment period (FIG. 1 A, $p > 0.05$ for both drug doses vs sham on week 5).

Figure 1B:
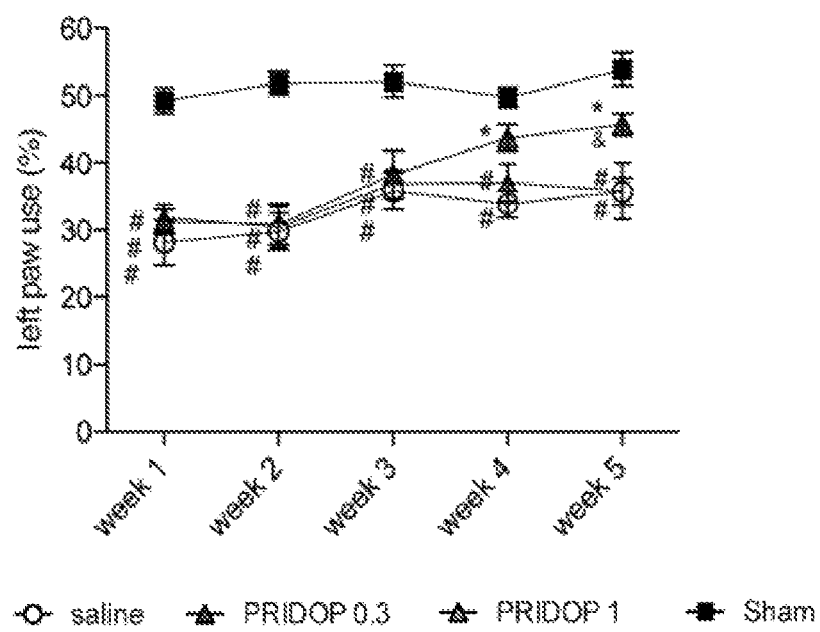
Figure 1C:
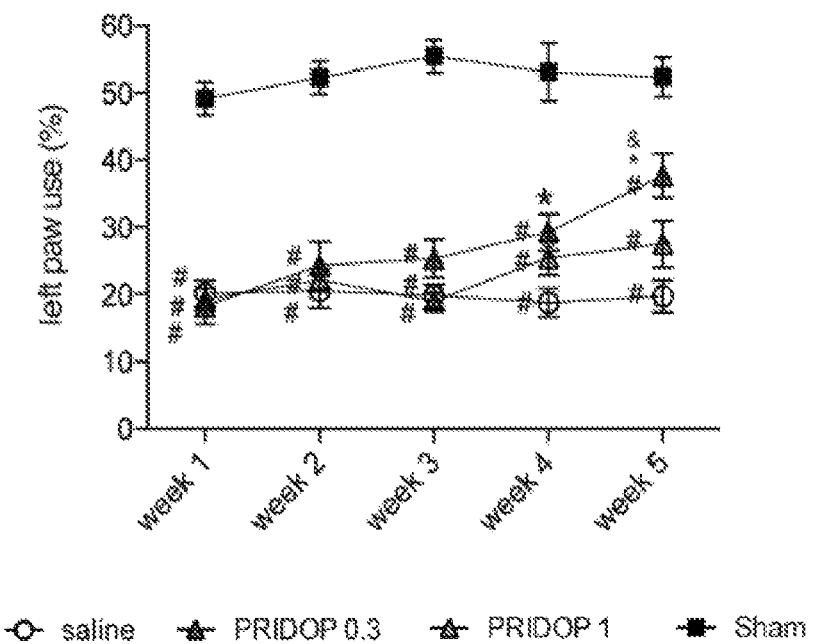

Furthermore, a difference was noticed between the 2 doses of pridopidine, as mice receiving the 0.3 mg/kg dose clearly diverged from saline-treated animals during most test sessions (*$p < 0.05$ for pridopidine 0.3 mg/kg vs saline at weeks 1-3), whereas mice treated with 1.0 mg/kg pridopidine differed from the saline group only on the first test session (see week in FIG. 1A, $p < 0.05$ for 1 mg/kg pridopidine vs saline). In the cylinder test, the 6-OHDA lesion yielded a similar deficit in the contralateral forelimb use in all treatment groups (see data from week 1 in FIG. 1B, ~40% difference and $p < 0.05$ vs sham in both saline- and pridopidine-treated mice). This significant difference from sham-lesion controls was maintained in all groups through the third week (FIG. 1B). Thereafter, mice treated with 0.3 mg/kg pridopidine showed a visible improvement, reaching levels of performance comparable with sham-control values on weeks 4 and 5 (FIG. 1B, week 4, $p < 0.05$ vs saline and $p > 0.05$ vs sham; week 5, $p < 0.05$ vs both saline and 1.0 mg/kg dose and $p > 0.05$ vs sham). In contrast, treatment with 1.0 mg/kg pridopidine did not restore contralateral forelimb use in the cylinder test (see week 5 in FIG. 1B, ~33% difference and $p < 0.05$ vs sham in both pridopidine-1 and saline group). Significant overall differences between groups and testing sessions were also found in the stepping test (FIG. 1C). The lesion-induced stepping deficit was initially severe in all groups (see data from week 1 in FIG. 1C, ~60% difference and $p < 0.05$ vs sham in both saline- and pridopidine-treated mice). All 6-OHDA-lesioned mice continued to show a significant deficit during the first 2 weeks regardless of treatment allocation. Thereafter, animals treated with 0.3 mg/kg pridopidine showed a gradual improvement, diverging significantly from the saline-treated group on weeks 4 and 5. Although not reaching sham control values, the performance of mice treated with 0.3 mg/kg pridopidine had improved by ~94% above the vehicle (saline by the end of the treatment period (see week 5 in FIG. 1C, $p < 0.05$ for pridopidine-0.3 vs both saline and pridopidine-1, $p > 0.05$ vs sham). Animals receiving 1.0 mg/kg pridopidine showed a trend towards an improved stepping performance during the last 2 weeks, but the difference from saline-treated mice did not reach significance (FIG. 1C, cf. pridopidine-1 and saline group in week 5, ~49% and ~63% difference vs sham, respectively, $p < 0.05$ for both comparisons).

Figure 2A:
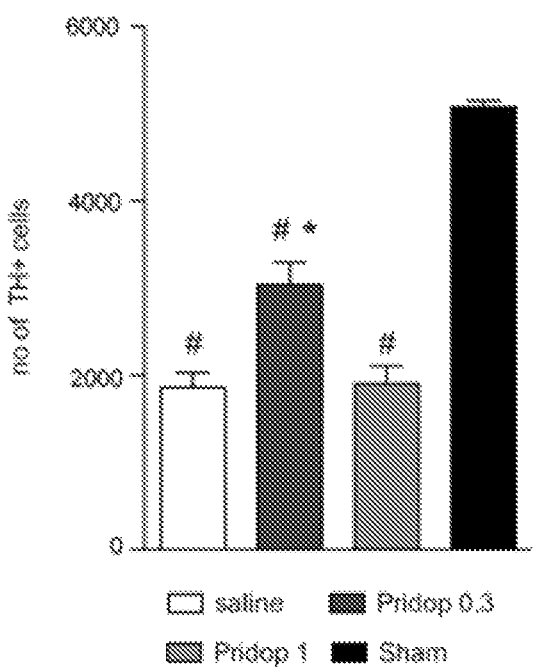
FIGS. 2A-2K Chronic treatment with pridopidine low dose (0.3 mg/kg), (but not with pridopidine high dose 1 mg/kg) induces neuro-histological restoration.
Figure 2B:
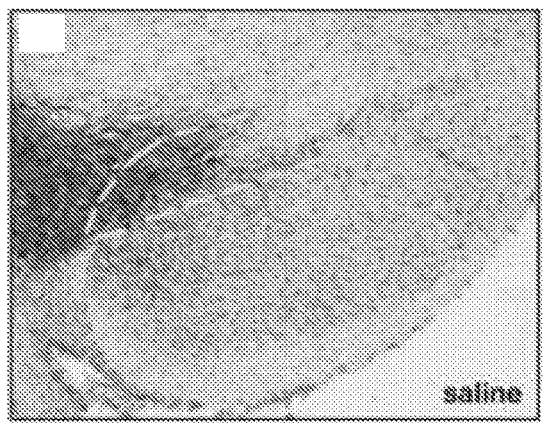
Figure 2C:
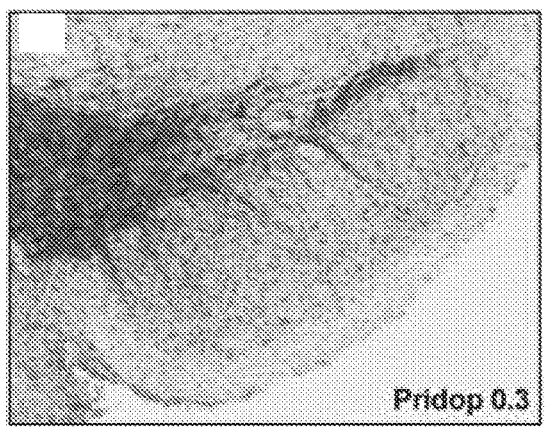
Figure 2D:
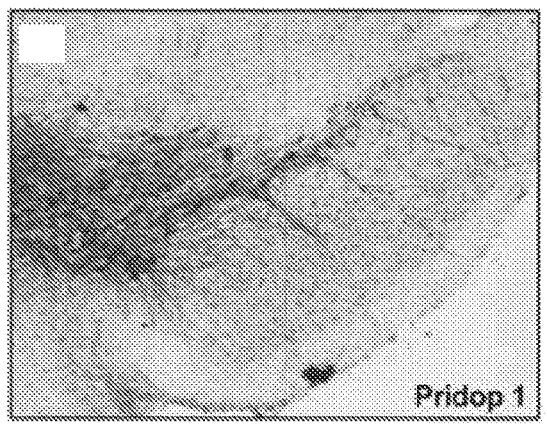
Figure 2E:
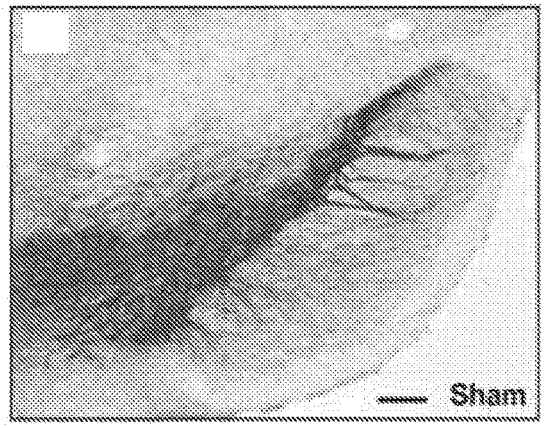

Example 2: Pridopidine has Neuroprotective and Neurorestorative Effects on Nigrostriatal Dopamine Neurons Unbiased stereology was used to count dopaminergic cell bodies in the SNc. On the side ipsilateral to the lesion, mice treated with saline displayed ~65% reduction in nigral TH-positive neurons (i.e., ~1960 cells in saline-treated mice vs ~5076 cells in sham-lesion controls, $p < 0.05$, FIG. 2A). Mice treated with 0.3 mg/kg pridopidine showed a significantly larger number of TH-positive neurons (3034 cells), corresponding to an increase by ~55% relative to saline treatment (FIG. 2A, *$p < 0.05$). The higher dose of pridopidine (1.0 mg/kg) did not, however, confer significant protection of dopaminergic cell bodies in SNc (~1901 cells counted; $p > 0.05$ vs saline), although it appeared to produce a larger density of TH-immunopositive neurites in the SN pars reticulata (cf. FIGS. 2B and D).

Figure 2F:
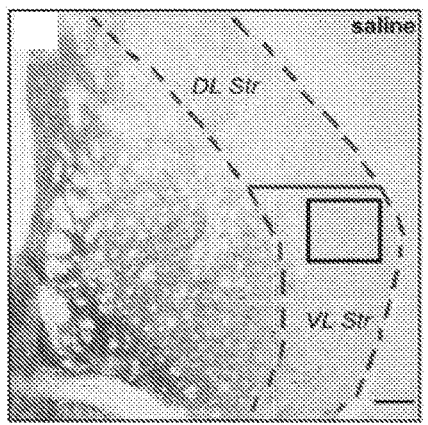
Figure 2F:
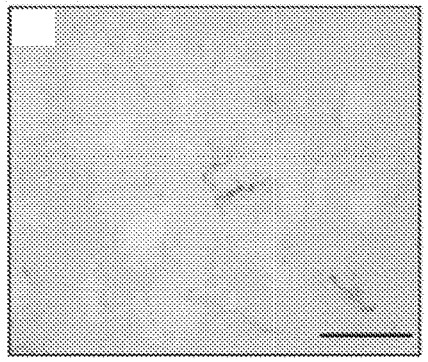

To examine the effects of pridopidine treatment on striatal DA innervation density, the TH-immunopositive axon fibers were measured at high magnification by randomly sampling an estimated 10% of the cross-sectional area over the lateral caudate-putamen (encased by hatched lines in FIG. 2F). This analysis could not be applied to sham-lesioned mice due to the impossibility to resolve distinct fibers in an intact striatum [Francardo V, Bez F, Wieloch T, Nissbrandt H, Ruscher K, Cenci 33. MA.; Song D D, Haber S N. Striatal responses to partial dopaminergic lesion: evidence for compensatory sprouting. The Journal of Neuroscience: The Official Journal of the Society for Neuroscience. 2000; 20(13):5102-14; Granado N, Ares-Santos S, Tizabi Y, Moratalla R. Striatal Reinnervation Process after Acute Methamphetamine-Induced Dopaminergic Degeneration in Mice. Neurotoxicity Research. 2018.].

Figure 2G:
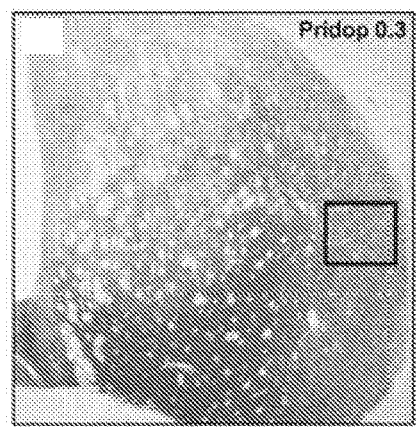
Figure 2G:
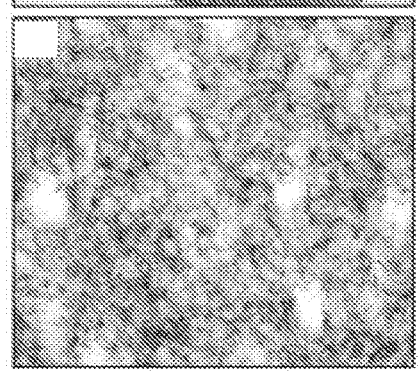
Figure 2H:
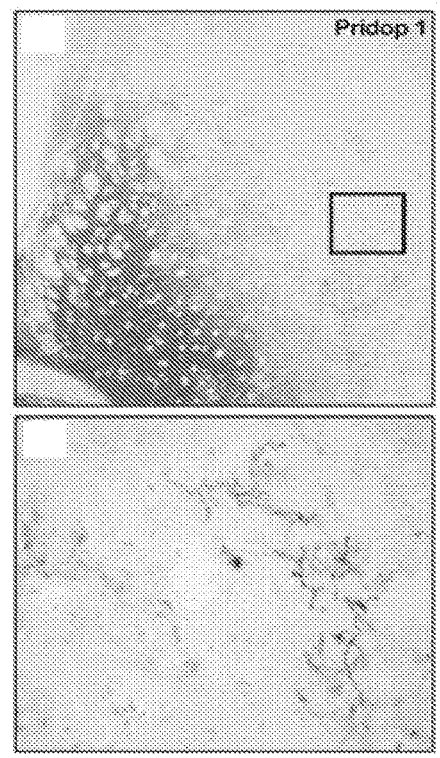
Figure 2I:
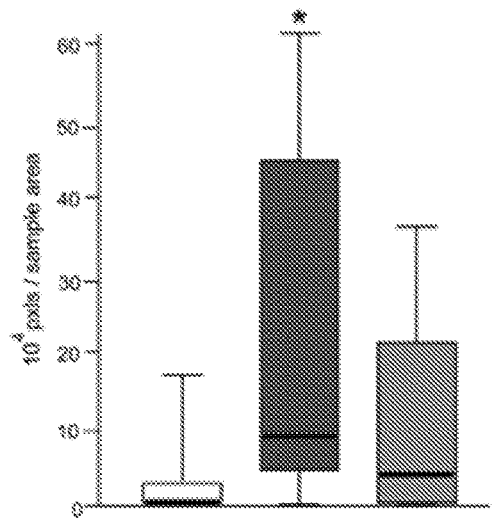
Figure 4A:
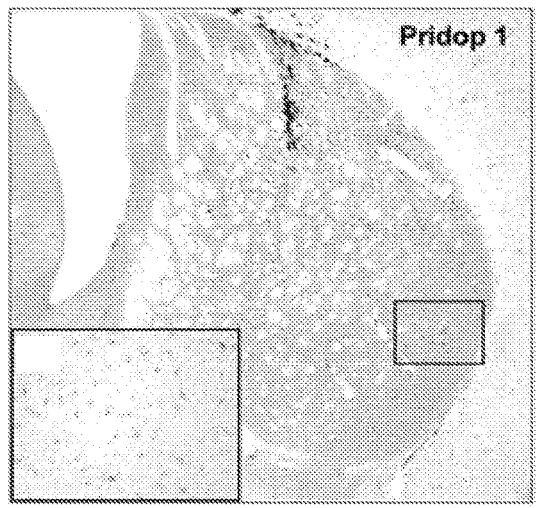
(FIG. 4A) spontaneous rotations: ANOVA p<0.0001 time, treatment, interaction, time F(4,104)=45.36, treatment F(2,26)=15.54, interaction F(8,104)=11.15.
Figure 4A:
Figure 4A:
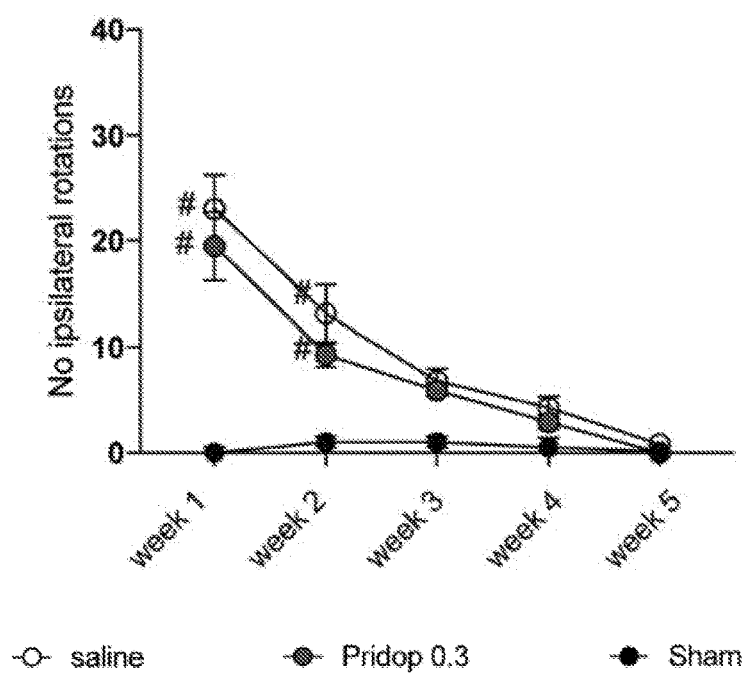

Chronic treatment with 0.3 mg/kg pridopidine markedly enhanced the number of TH fiber profiles (cf. FIGS. 2F and 4G), yielding an increase by about 15-fold in median values relative to those of saline-injected animals (FIG. 2I, $p < 0.05$). All animals treated with pridopidine 0.3 mg/kg showed and abundance of thick and highly branched axons harboring enlarged varicosities (FIG. 2G'), indicative of a sprouting response [Song D D, Haber S N. Striatal responses to partial dopaminergic lesion: evidence for compensatory sprouting. The Journal of Neuroscience: The Official Journal of the Society for Neuroscience. 2000; 20(13):5102-14; Granado N, Ares-Santos S, Tizabi Y, Moratalla R. Striatal Reinnervation Process after Acute Methamphetamine-Induced Dopaminergic Degeneration in Mice. Neurotoxicity Research. 2018]. Although clearly less abundant, similar morphologicalfeatures were also encountered in mice treated with 1.0 mg/kg pridopidine (FIG. 2H-H'), but the effect of this larger dose did not achieve statistical significance (FIG. 2I, $p > 0.05$ forpridopidine-1 vs saline).

Figure 2J:
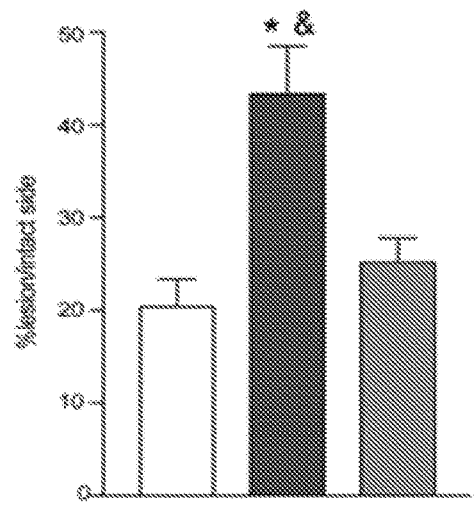
Figure 2K:
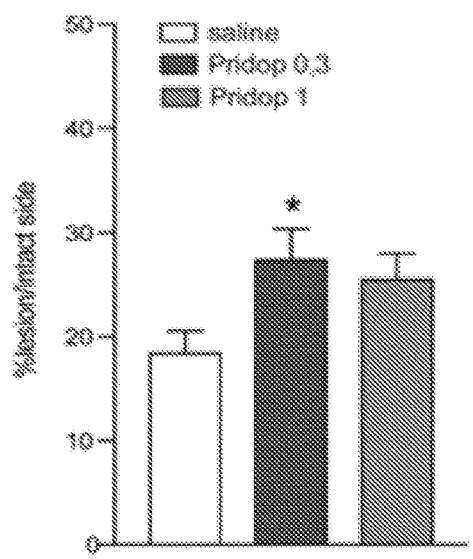

A gross estimate of DA innervation levels was obtained by measuring the O.D. of TH immunostaining in the ventrolateral and dorsolateral striatum through the entire extent of these regions (FIG. 2J, K). In the ventrolateral striatum, treatment with 0.3 mg/kg pridopidine yielded a greater than twofold increase in TH O.D. above saline control levels ($p < 0.05$) (FIG. 2J). Mice treated with 1 mg/kg pridopidine showed a trend towards an increase that did not reach statistical significance (FIG. 2J). Animals treated with 0.3 pridopidine showed a significant, albeit smaller increase in TH O.D. also in the dorsolateral striatum, while animals treated with 1 mg/kg pridopidine showed, again, only a trend (FIG. 2K). Taken together, these results indicate that treatment with 0.3 mg/kg pridopidine had provided partial protection of nigral DA cell bodies, accompanied by a marked dopaminergic reinnervation of the highly depleted lateral striatum. The latter effect was particularly prominent in the ventrolateral quadrant, a region controlling forelimb use in rodents [Chang J W, Wachtel S R, Young D, Kang U J. Biochemical and anatomical characterization of forepaw adjusting steps in rat models of Parkinson's disease: studies on medial forebrain bundle and striatal lesions. Neuroscience. 1999; 88(2):617-28; Cousins M S, Salamone J D. Skilled motor deficits in rats induced by ventrolateral striatal dopamine depletions: behavioral and pharmacological characterization. Brain Research. 1996; 732(1-2):186-94]. The larger dose of pridopidine (1 mg/kg) did not achieve significant effects on any parameter.

Figure 3A:
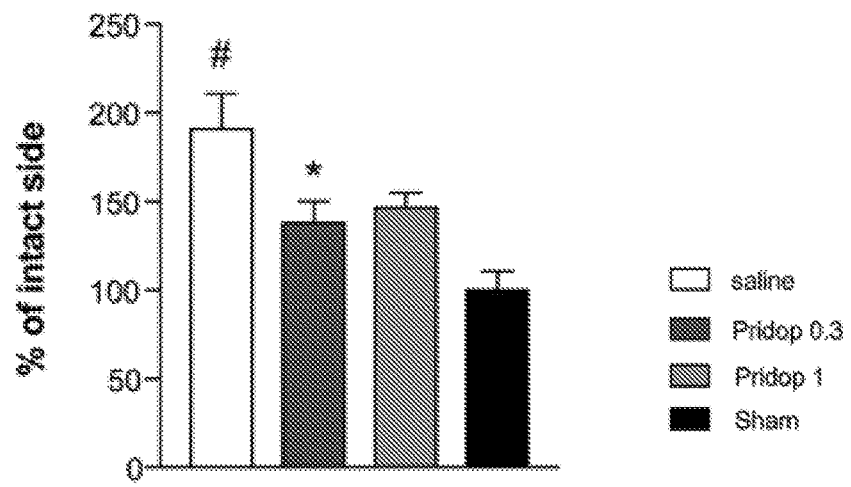
(FIG. 3A) One-way ANOVA p=0.0002, F (3,28)=9.005.
Figure 3B:
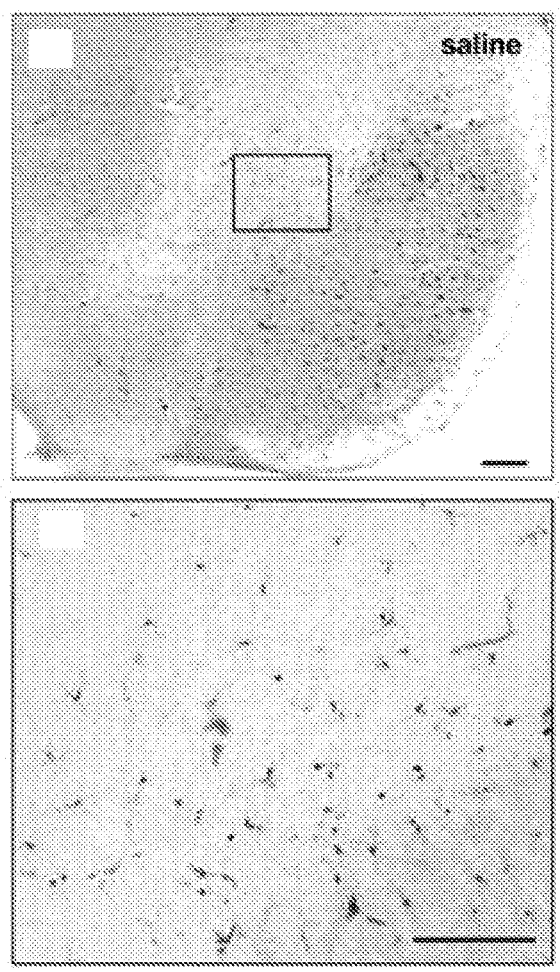
FIG. 3 Pridopidine low dose (0.3 mg/kg) but not high dose (1 mg/kg) treatment reduces microglia activation in the nigrostriatal pathway. Counts of CD68-positive microglial cells in the SNc (FIG. 3A) and ventrolateral striatum (FIG. 3F) and corresponding photomicrographs (FIG. 3B-J'). Mice receiving 0.3 mg/kg pridopidine showed a significantly lower number of CD68-positive cells compared to saline-treated controls at both nigral and striatal levels. Low-magnification photomicrographs (FIG. 3B-J) were taken under a ×4 objective, whereas insets (B'-J') were photographed under a ×20 objective. Scale bars, 100 µm.
(FIG. 3F) one-way ANOVA p=0.0005, F (3,28)=8.049. Post hoc Tukey test, p<0.05 asterisk, versus saline; number sign, versus sham.

The neurorestorative effects of pridopidine treatment was studied whether it coincided with a reduced microglial activation in the involved regions. To this end, we counted the number of CD68-immunopositive microglial cells in the SNc and the ventrolateral striatum. This number was significantly reduced in both regions in mice treated with 0.3 mg/kg pridopidine (FIG. 3A, F; $p<0.05$ for pridopidine-0.3 vs saline, $p>0.05$ vs sham). Mice treated with the larger dose of pridopidine showed a trend towards an effect in the SNc (FIG. 3A; $p>0.05$ vs sham), but not in the ventrolateral striatum (FIG. 3F; $p<0.05$ vs sham, $p>0.05$ vs saline).

Example 3: Treatment with Pridopidine is not Effective in Sigma-1 KO Mice

Figure 4B:
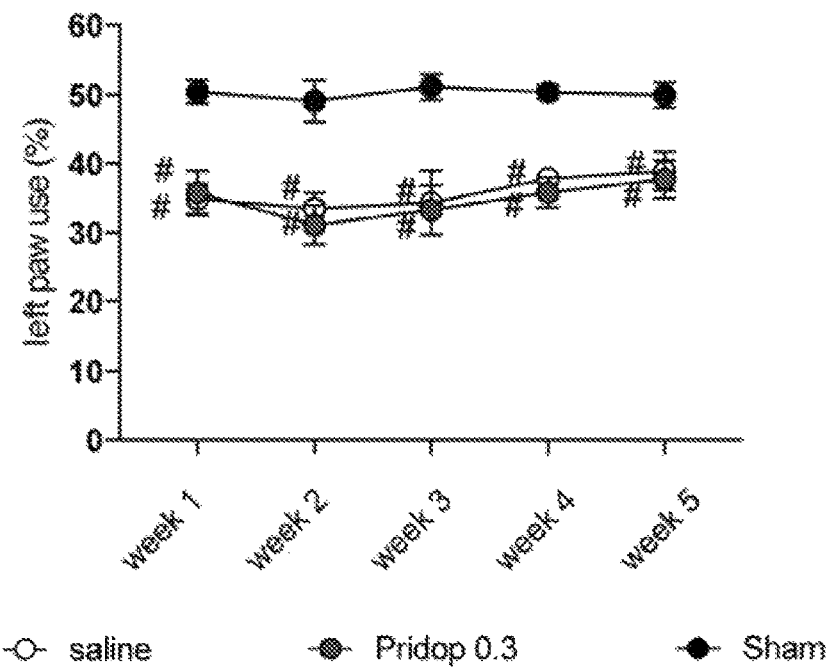
(FIG. 4B) cylinder test: ANOVA p>0.05 time and interaction, p<0.0001 treatment, time F(4,104)=1.23, treatment F(2,26)=1.76, interaction F(8,104)=0.32.
Figure 4C:
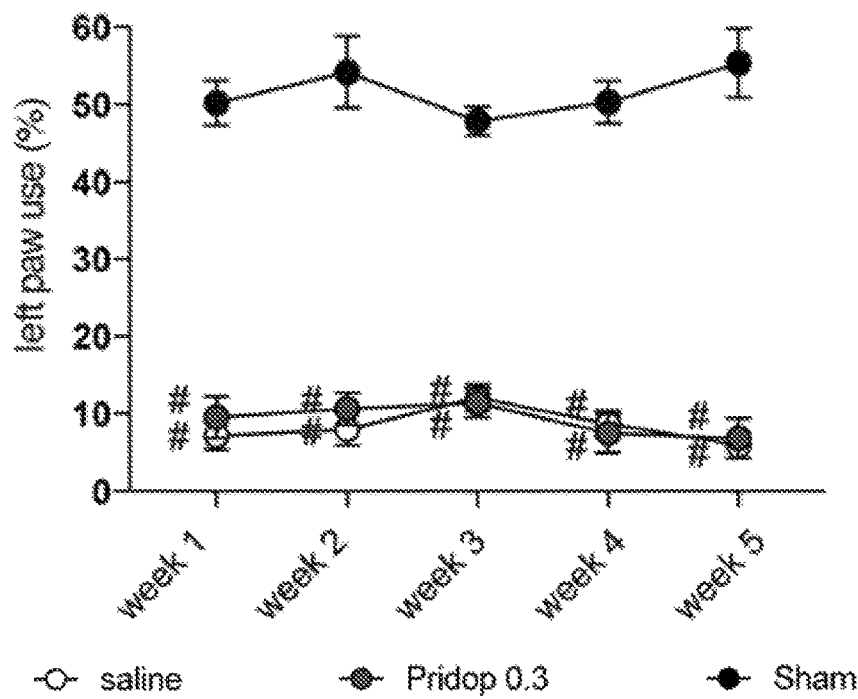
(FIG. 4C) stepping test: ANOVA p>0.05 time and interaction, p<0.0001 treatment, time F(4,104)=0.46, treatment F(2,26)=346.4, interaction F(8,104)=1.35; p<0.05, number sign versus "sham".
Figure 5A:
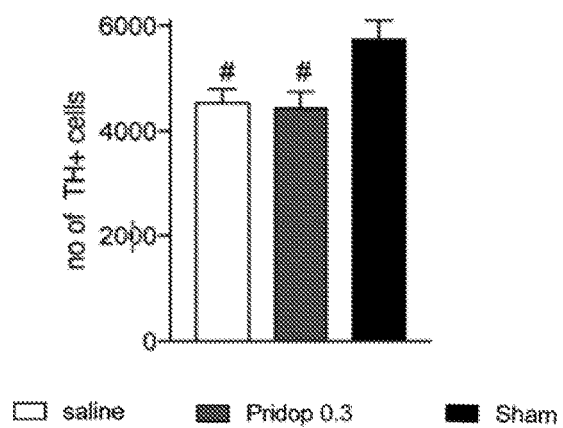
FIG. 5 Pridopidine low dose (0.3 mg/kg) is devoid of neurorestorative effects in 6-OHDA-lesioned mice that lack S1R.
(FIG. 5F-5G) Optical density (O.D.) of TH immunostaining over the entire cross-sectional area of ventrolateral (FIG. 5F) and dorsolateral (FIG. 5G) striatum. O.D. values from the side ipsilateral to the lesion are expressed as a percentage of those from the contralateral intact side in each animal (mean±SEM from 4 sections per animal throughout the striatum).
(FIG. 5H-5I') Representative photomicrographs of TH-immunostained striatal sections from a saline-treated (FIG. 5H, 5H') and a pridopidine-0.3 mg/kg treated S1R KO mouse (FIG. 5I, 5I'). Scale bar, 200 µm.
Figure 5B:
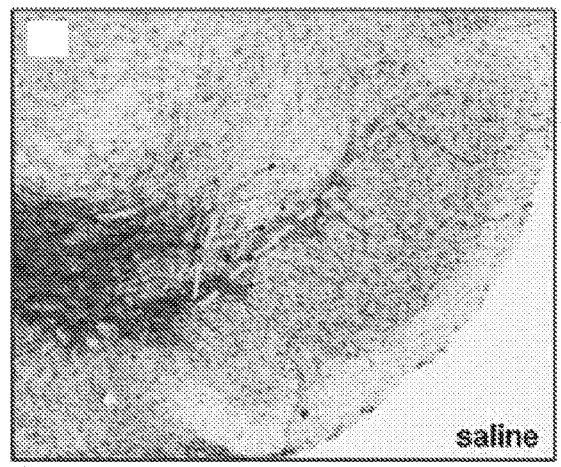
Figure 5C:
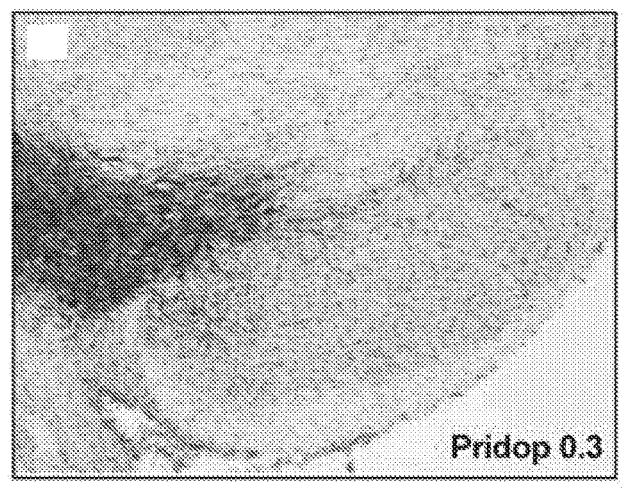
Figure 5G:
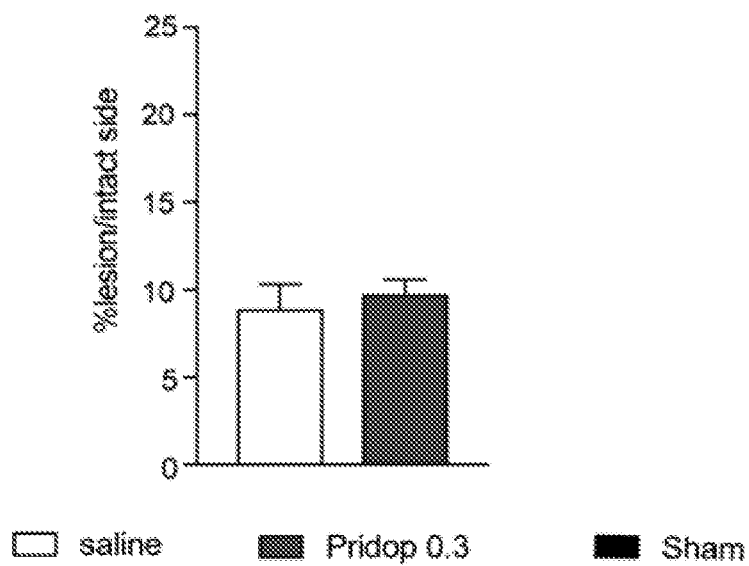
Figure 5H:
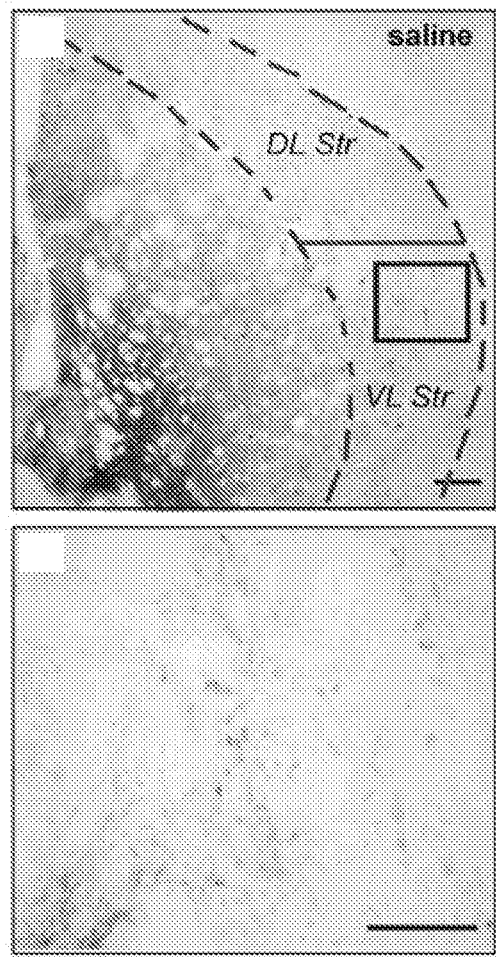
Figure 5I:
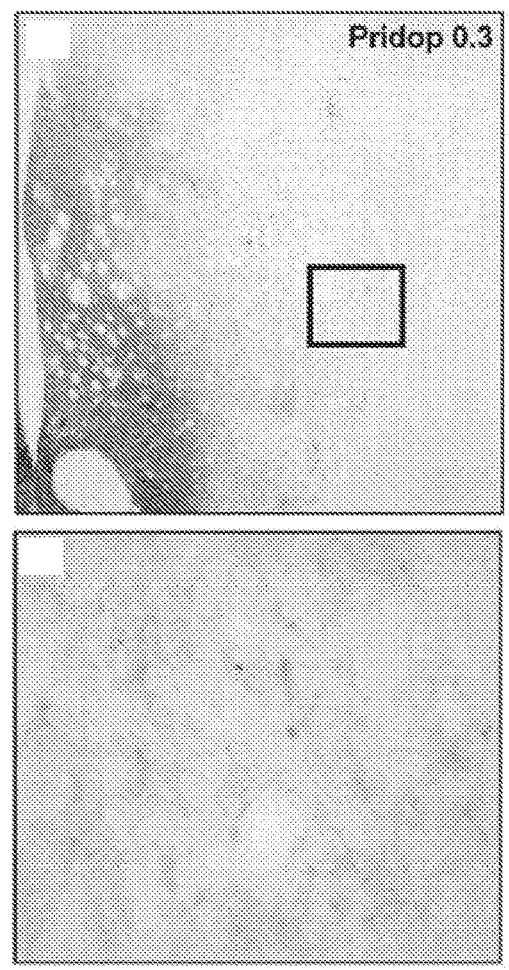

The effective dose of pridopidine (0.3 mg/kg) in S1R KO mice sustaining 6-OHDA lesions or sham lesions was studied. S1R KO-lesioned mice treated with either 0.3 mg/kg pridopidine or saline showed similar levels of spontaneous rotations (FIG. 4A) and forelimb use asymmetry in cylinder test (FIG. 4B) and stepping test (FIG. 4C) throughout the 5 weeks of treatment ($p>0.05$ for pridopidine vs saline in all tests and sessions). Moreover, treatment with pridopidine did not have any effect on either nigral DA neurons (FIG. 5A) or striatal TH fiber density (FIG. 5E-G) ($p>0.05$ for pridopidine vs saline on all parameters). These data clearly indicate that, in the absence of S1R, pridopidine cannot exert any restorative action on the damaged nigrostriatal DA pathway.

An interesting collateral finding of this experiment is that S1R KO mice had responded to the 6-OHDA lesion with a distinctive pattern of nigrostriatal damage. Indeed, compared to wild-type animals, 6-OHDA-lesioned S1R KO mice featured a milder loss of DA cell bodies in the SNc (~22% instead of ~61% loss, cf. saline groups in FIG. 2A vs. FIG. 5A), but a lower density of TH fibers in the lateral striatum (median value of 899 vs 5842 fiber pixels/sample area in KO vs wild-type mice, cf. saline groups in FIG. 2I vs FIG. 5E).

A more severe degeneration of striatal dopaminergic fibers compared to nigral cell bodies in S1R KO mice is likely to account for apparent differences in lesion-induced motor impairments relative to the wild-type genotype, in particular, the less severe rotational bias concurring with a more severe deficit in forelimb stepping (cf. FIGS. 1 and 4).

Example 4: Pridopidine Upregulates Neurotrophic Factors and Activates ERK1/2 in the Striatum The gradual improvement in forelimb use and the concomitant increase in striatal DA fibers density induced by pridopidine 0.3 mg/kg are indicative of a neurorestorative action mediated by trophic factors, whose brain levels can increase upon pharmacological stimulation of S1R [Penas C, Pascual-Font A, Mancuso R, Fores J, Casas C, Navarro X. Sigma receptor agonist 2-(4-morpholinethyl)1 phenylcyclohexanecarboxylate (Pre084) increases GDNF and BiP expression and promotes neuroprotection after root avulsion injury. Journal of Neurotrauma. 2011; 28(5):831-40; Francardo V, Bez F, Wieloch T, Nissbrandt H, Ruscher K, Cenci 33. MA. Fujimoto M, Hayashi T, Urfer R, Mita S, Su T P. Sigma-1 receptor chaperones regulate the secretion of brain-derived neurotrophic factor. Synapse. 2012; 66(7):630-9].

Figure 6A:
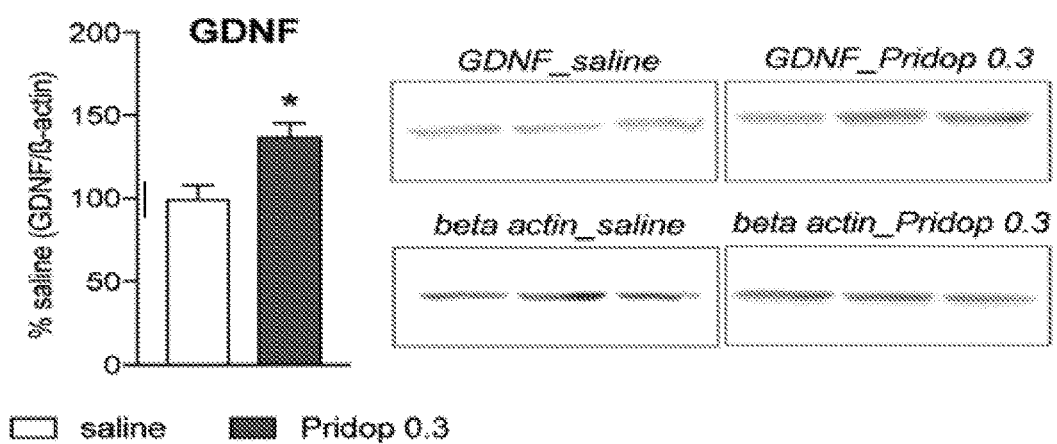
(FIG. 6A) GDNF p=0.003.
Figure 6B:
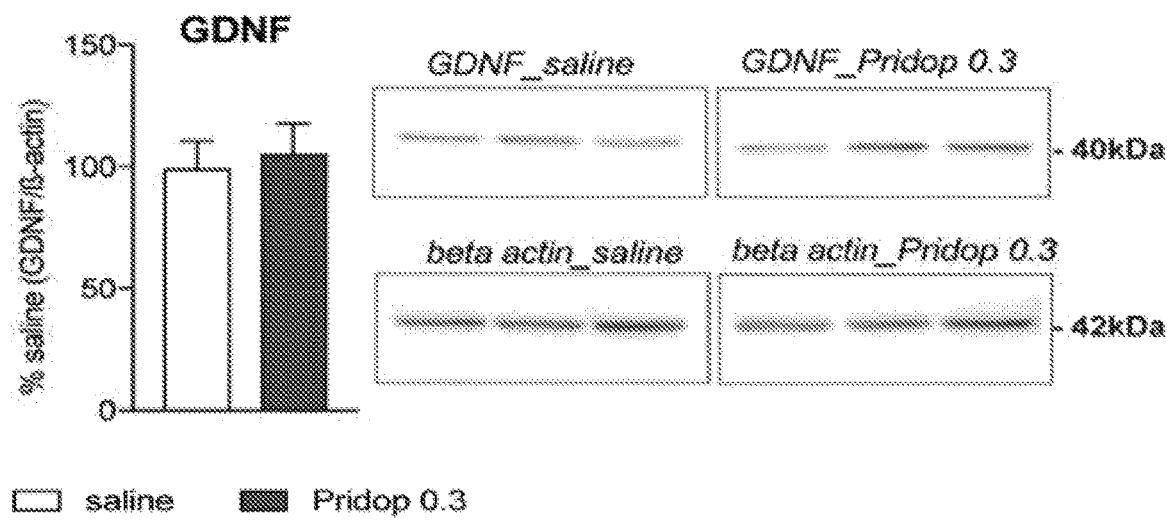
(FIG. 6B) BDNF p=0.013, (FIG. 6C) pERK1/2 p=0.049; substantia nigra.
Figure 6C:
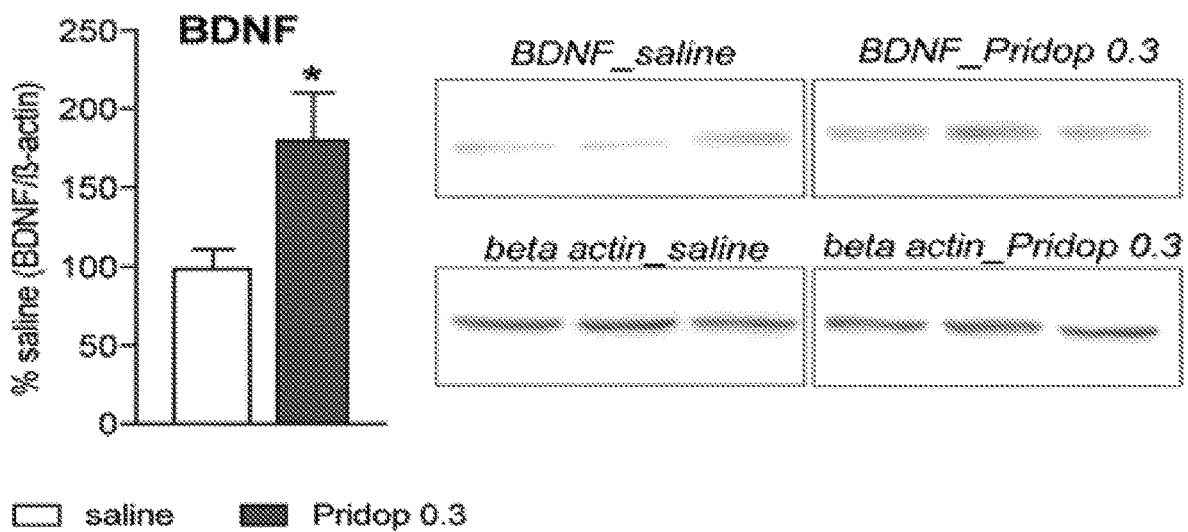
FIG. 6 Treatment with 0.3 mg/kg pridopidine upregulates trophic factors and phosphorylated ERK1/2. Western blot analysis of GDNF, BDNF, and phosphorylated ERK1/2 (pERK) using striatal samples (FIG. 6A-6C) and nigral samples (FIG. 6D-6E) from 6-OHDA-lesioned wild-type mice treated with 0.3 mg/kg pridopidine (n=9) or saline solution (n=11) for 5 weeks. Results are normalized for β-actin levels, and data from pridopidine-treated animals are shown as a percentage of the values from saline-treated controls. Unpaired t test, striatum.
(FIG. 6D) GDNF p=0.72.
(FIG. 6E) BDNF p=0.0008.
(FIG. 6F) pERK1/2 p=0.106.
Figure 6D:
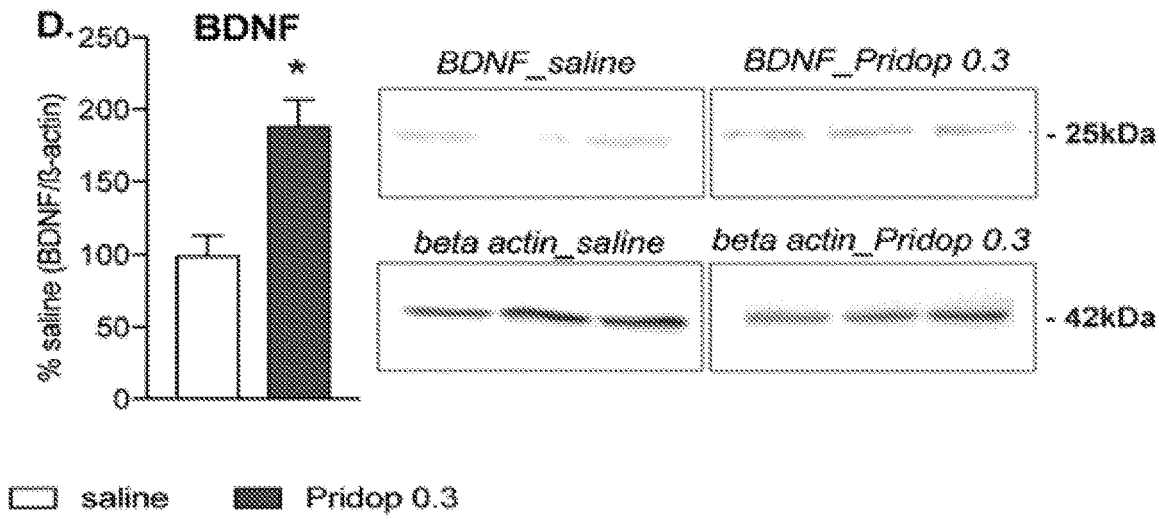
Figure 6E:
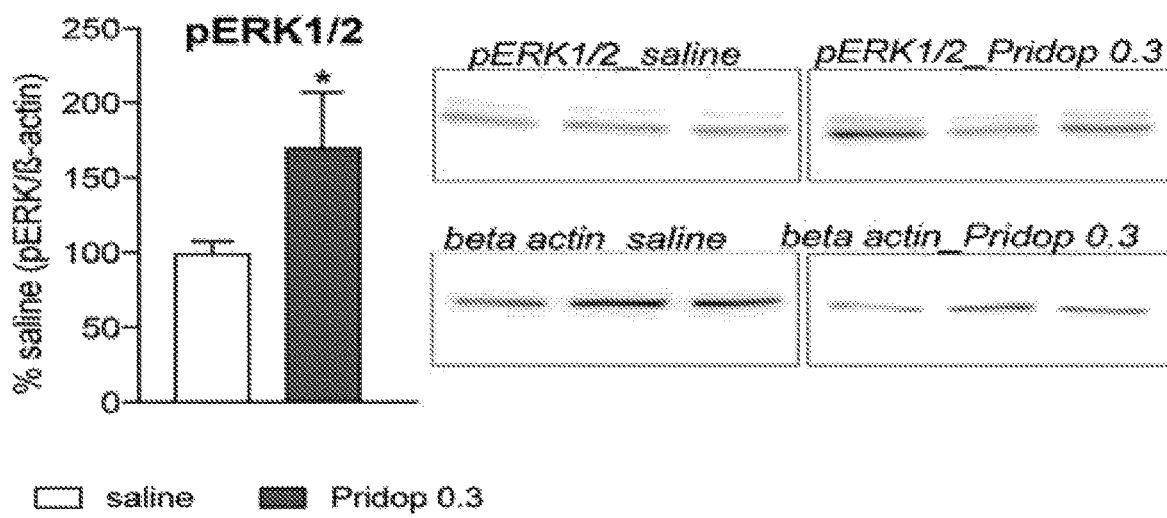
Figure 6F:
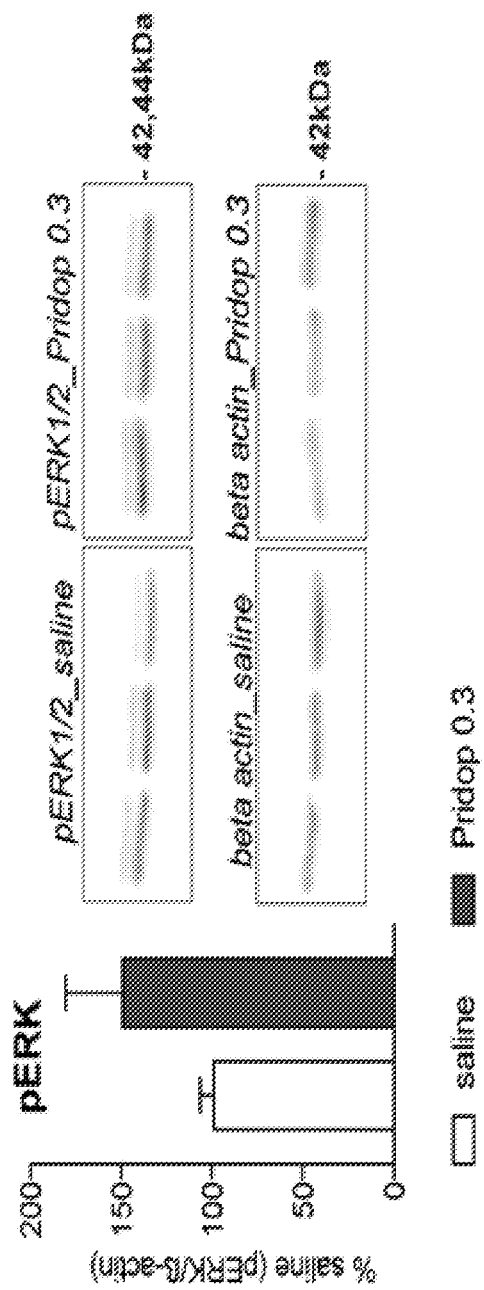

Western blot analysis of GDNF, BDNF, and phosphorylated ERK1/2 (a major intracellular effector of neurotrophin signaling [Garcia-Martinez J M, Perez-Navarro E, Gavalda N, Alberch J. Glial cell line-derived neurotrophic factor promotes the arborization of cultured striatal neurons through the p42/p44 mitogen-activated protein kinase pathway. Journal of Neuroscience Research 2006; 83(1):68-79]) was therefore carried out in additional groups of wild-type mice sustaining intrastriatal 6-OHDA lesions followed by a 35-day treatment with 0.3 mg/kg pridopidine or saline. Pridopidine promoted a significant striatal upregulation of GDNF and BDNF levels (+37.6% and +80.8% vs saline, respectively, $p<0.05$ for both markers, FIG. 6A, C). In the SN, only BDNF levels showed a significant increase (+88.5% vs saline, FIG. 6D, $p<0.05$). Treatment with pridopidine 0.3 mg/kg also produced an increase in striatal and nigral levels of phosphorylated ERK1/2 (FIG. 6E, F), which reached significance only in the striatum (+71% vs saline, $p<0.05$, FIG. 6E).

The effect profile of the lower drug dose (0.3 mg/kg) includes both protection of nigral DA cell bodies and restoration of dopaminergic fiber density in the lateral striatum. In this region, the TH-positive fiber network exhibited morphological features typical of regenerating axons. Along with these morphological observations, the gradual restoration of forelimb use (which became significant only after 4 weeks of pridopidine treatment) points to a stimulation of DA axon terminal sprouting as a pivotal mechanism of functional recovery. This interpretation is further supported by the significant upregulation of GDNF, BDNF, and phosphorylated ERK1/2 produced by 0.3 mg/kg pridopidine in the striatum. These factors strongly stimulate neuritic outgrowth from nigrostriatal DA neurons both in vitro and in vivo.

The higher dose of pridopidine (1 mg/kg) was overall ineffective on most behavioral and neuro-histological endpoints. A definite proof that the neurorestorative effects of 0.3 mg/kg pridopidine depended on S1R was obtained by evaluating this dose in S1R.

Example 5: Pridopidine Pharmacokinetics in Mice

Pharmacokinetics of Pridopidine in the Mouse

In a first pharmacokinetics (PK) study, pridopidine was given orally (p.o., which is the administration route used in humans). In this study, 4 doses of pridopidine (0.3, 3, 10, and 30 mg/kg, N=24 per dose), were administered to male C57B16 mice for 7 days via oral gavage. Blood and brain samples were collected from 3 different mice per dose group per time point at the following times: prior to (t=−10 min) and 15 min, 30 min, 1 h, 2 h, 4 h, 6 h, and 8 h post drug administration. A second study was carried out to compare the drug's PK profile between oral (p.o.) and subcutaneous (s.c.) administration. Here, PK was examined following 7 daily administrations of 30 mg/kg pridopidine (HCl salt equivalents in water) either orally or subcutaneously (N=24 mice per administration route). Blood and brain samples were collected from 3 animals per route per time point, at the following time points: predose, 15 min, 30 min, 1 h, 2 h, 4 h, 6 h, and 8 h post last dose.

Plasma samples were placed into $K_3$-EDTA tubes (Becton-Dickinson, Mississauga, ON, Canada) and centrifuged for 5 min at 1500 g. Brain tissue was collected and frozen without further process. Prior to analysis pre-weighed brain samples were diluted and homogenized with 0.01 M phosphate buffer containing 0.32 M sucrose, pH 7.4 in a ratio of 1 g of 330 brain to 4 mL of homogenization solution.

Quantification of Pridopidine Plasma and Brain Concentrations and Pharmacokinetic Analysis Pridopidine and its internal standard, ACR354 (4-(3-methylsulfonyl)phenyl)-1-(propyld7)-piperidinium chloride), were extracted from EDTA plasma as well as from mouse brain homogenate (1:3 in phosphate-buffered saline, pH 7.4) by liquid-liquid extraction into acetonitrile. In brief, LC-MS/MS analyses were performed on a Shimadzu LC-20AD pump equipped with a Shimadzu SIL-20AC autosampler and Shimadzu CTO-20AC column oven. The MS/MS system was an MDS Sciex API-5000 mass spectrometer with an electrospray ionization probe (Toronto, Canada).

Chromatographic separation of the analytes was achieved on Phenomenex, Synergi 2.5μ Hydro-RP column. The linearity was from 2 to 3000 ng/mL with a lower limit of quantification (LLOQ) of 2 ng/mL in plasma and 2 to 3000 ng/mL with an LLOQ of 2 ng/mL in brain homogenate of 0.3- and 3-mg/kg-dose groups and 25 to 20,000 ng/mL in plasma and 75 to 60,000 ng/mL in brain homogenates, with LLOQ of 2 ng/mL and 75 ng/mL, respectively, for the higher doses. The deviation of pridopidine concentrations from quality control (QC) sample nominal concentration (accuracy values) was lower than 15% for all calibration curves. PK parameters were calculated using group mean concentration-time data, according to nominal time, that is, within ±5% from the scheduled time point, by noncompartmental modeling for extravascular administration using WinNonlin 6.3. Dose-normalized exposure was used in order to estimate pridopidine exposure following 1 mg/kg dose (see Table 1).

Table 1: Plasma and brain exposure following pridopidine administration to C57B16 mice. Table shows concentrations of pridopidine in plasma and brain after administration of ascending pridopidine doses (0.3, 1, 3, 10, and 30 mg/kg). The maximal Q3 concentration (Cmax) is expressed in nanograms per milliliter and micromolar. The AUC (area under curve, corresponding to the amount of pridopidine reaching the systemic circulation after a specific dose) is expressed as ng*hour/mL and in pM*hour. Each data point represents an average value obtained from 3 mice. Parameters for the 1-mg/kg dose are extrapolated based on average Cmax/dose and AUC0-last/dose values for 0.3, 3, 10, and 30 mg/kg groups.

TABLE 1

Plasma and brain exposure following pridopidine administration to C57B16 mice. Table shows concentrations of pridopidine in plasma and brain after administration of ascending pridopidine doses (0.3, 1, 3, 10, and 30 mg/kg). The maximal Q3 concentration (Cmax) is expressed in nanograms per milliliter and micromolar. The AUC (area under curve, corresponding to the amount of pridopidine reaching the systemic circulation after a specific dose) is expressed as ng*hour/mL and in pM*hour. Each data point represents an average value obtained from 3 mice. Parameters for the 1-mg/kg dose are extrapolated based on average Cmax/dose and AUC0-last/dose values for 0.3, 3, 10, and 30 mg/kg groups.

| Dose [mg/kg] | $C_{max}$ [ng/mL] | $C_{max}$ [μM] | $AUC_{0\text{-}last}$ [ng*h*/mL] | $AUC_{0\text{-}last}$ [μM*h] | $T_{max}$ [h] |
|---|---|---|---|---|---|
| Plasma | | | | | |
| 0.3 | 22 | 0.08 | 26 | 0.09 | 0.25 |
| 1[1)] | 109 | 0.4 | 116 | 0.4 | NA |
| 3 | 277 | 1.0 | 406 | 1.4 | 0.5 |
| 10 | 1369 | 4.9 | 936 | 3.3 | 0.25 |
| 30 | 2577 | 9.2 | 3101 | 11.0 | 0.25 |
| Brain | | | | | |
| 0.3 | 110 | 0.39 | 120 | 0.43 | 0.25 |
| 1[1)] | 331 | 1.2 | 392 | 1.4 | NA |
| 3 | 763 | 2.7 | 1051 | 3.7 | 0.25 |
| 10 | 3506 | 12.5 | 2971 | 10.6 | 0.5 |
| 30 | 6396 | 22.7 | 10836 | 38.5 | 0.25 |

1) Estimated Value

Pridopidine presented similar plasma and brain PK following oral and subcutaneous single-dose administrations, with a relative oral/subcutaneous exposure ratio of 117% for Cmax and 90% for $AUC_{0-t}$ in plasma, and 88% for Cmax and 96% for $AUC_{0-t}$ in brain tissue. Thus, pridopidine exposure data following oral dosing fairly represent the exposure achieved by subcutaneous administration. A dose-response PK study after oral administration indicated that the drug's plasma and brain exposure was dose-proportional (Table 1). Brain-to-plasma ratio measurements showed that pridopidine concentrations were four- to fivefold larger in the brain than in plasma for the 0.3-mg/kg dose and two- to threefold larger for the dose range 1 to 30 mg/kg (cf. Cmax and AUC values in the brain vs plasma, Table 1).

Administration of 0.3 and 1 mg/kg pridopidine yielded brain Cmax values of 110 and 331 ng/mL (corresponding to 390 nM and 1200 nM), respectively, occurring at a median Tmax of 0.25 h and with corresponding $AUC_{0-last}$ values of 120 and 392 ng*h/mL (corresponding to 0.43 and 1.4 h*μM) Pridopidine was rapidly cleared with brain total levels close to 3 ng/mL (corresponding to 11 nM, out of which only ~2 nM are free) already after 3 h. The free fraction of pridopidine was determined using a commercially available in vitro protein binding assay. At the doses of 0.3 and 1 mg/kg, the unbound (free) fraction of pridopidine in brain tissue was estimated to be ~50%. Therefore, brain free pridopidine concentrations at Cmax were estimated to correspond to 55 and 165.5 ng/mL (or 195 nM and 600 nM) for the doses of 0.3 and 1 mg/kg, respectively. Based on the reported binding affinity of pridopidine to the rat S1R (Ki 69.7 nM, [Sahlholm K, Arhem P, Fuxe K, Marcellino D. The dopamine stabilizers ACR16 and (−)-OSU6162 display nanomolar affinities at 42. the sigma-1 receptor. Molecular Psychiatry. 2013; 18(1): 12-4.]), it thus seems plausible that, at Cmax, both doses of 0.3 and 1 mg/kg pridopidine would yield 100% occupancy of the S1R. This concentration indicates that at this dose these is selective binding for the sigma-1 receptor only.

Example 6: GCase Activity is Reduced in GBA-Associated PD

GBA encodes the lysosomal hydrolase glucocerebrosidase (GCase). GCase activity was measured in human control fibroblasts, fibroblasts from PD patients with heterozygous GBA mutations (N370S/wt and L444P/wt) and fibroblasts from idiopathic (sporadic) PD patients (iPD). GCase activity was shown to be significantly decreased in N370S/wt and L444P/wt fibroblasts by 32% and 35%, respectively. No loss of GCase activity was found in iPD fibroblasts, thus PD associated with GBA deficiency involves different mechanisms of action (Sanchez-Martinez et al. 2016).

Example 7: ER Stress

Accumulation of Misfolded Proteins Leads to ER Stress in Mutant GBA Dopaminergic Neurons Accumulation of misfolded proteins in the ER can overload the cellular capacity for protein re-folding and induce ER stress. In Fernandes et al., dopaminergic neurons were differentiated from human induced pluripotent stem cells (iPSCs) taken from healthy controls and PD patients with the GBA-N370S mutation. Levels of the two ER-resident chaperone proteins, Bip/GRP78 and calreticulin reveal significant upregulation in GB A-N370S dopaminergic neuronal cultures when compared with control-derived dopaminergic cultures, indicating an increase in ER stress (Fernandes et al. 2016).

Pridopidine Decreases mHtt-Induced ER Stress

Figure 7:
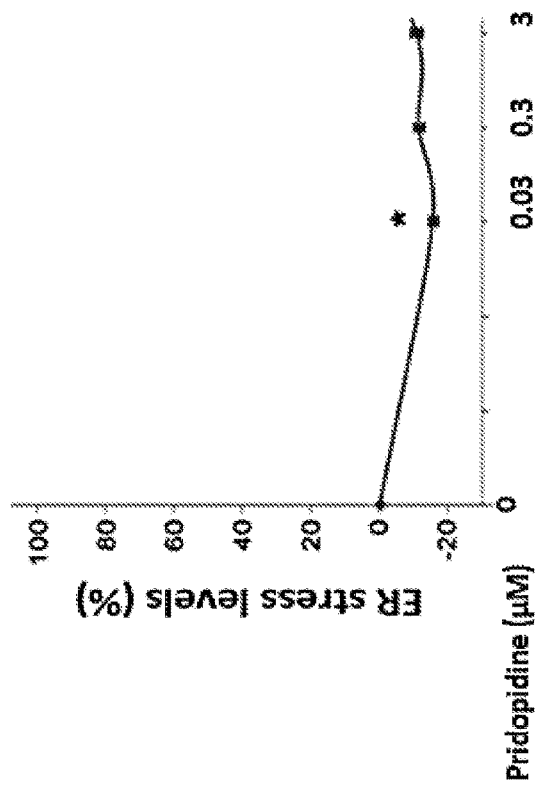
FIG. 7 Dose-dependent reduction of early mHtt-induced ER stress by Pridopidine. H2a-GFP was transiently co-expressed with Htt20Q-mCherry or Htt96Q-mCherry (exon 1) in STHdhQ7/7 cells. H2a-GFP aggregation is a marker of cell stress. Cells were treated without or with increasing concentrations of pridopidine (from 0.03 to 3 µM equivalent to 0.01 µg/ml to 1 µg/ml) starting 4 h post-transfection and imaged in a confocal microscope 24 h post-transfection. Images of individual cells (~150 cells per experiment) with Htt96Q-mCherry aggregates or with Htt20Q-mCherry were quantified compared to untreated cells with and without aggregates. For comparative purposes, 100% represents H2a-GFP relative intensity in untreated cells showing Htt96Q-mCherry aggregates, 0% is H2a-GFP relative intensity in untreated cells without Htt96Q-cherry aggregates. The graphs are averages of 3 experiments +−SE. The asterisks indicate P values compared to untreated, <0.05 (*) and <0.01 (**).
Figure 7:
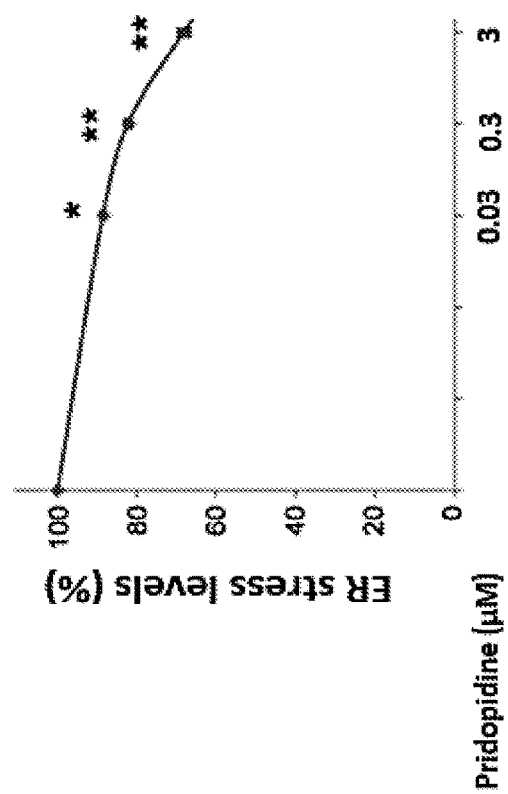

STHdhQ7/7 cells transfected with the mutant Htt96Q-mCherry (expanded) construct show visible Htt96Q-mCherry aggregates (typically one large aggregate per cell) together with high levels of accumulated H2a-GFP indicative of ER stress. STHdhQ7/7 cells expressing Htt20Q-mCherry (normal) or Htt96Q-mCherry without visible aggregates show low levels of H2a-GFP (no ER stress). Pridopidine significantly reduces H2a-GFP accumulation in cells positive for mHtt aggregates in a dose-dependent manner, and does not alter H2a-GFP levels in cells without aggregates or in cells expressing Htt20Q-mCherry (FIG. 7). Thus, pridopidine decreases Htt-induced ER stress in a dose-dependent manner.

Figure 8:
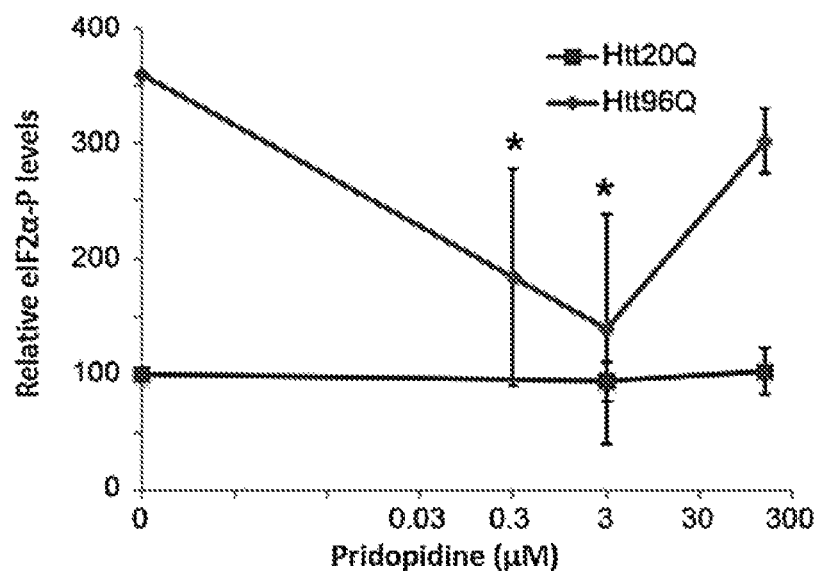
FIG. 8 Pridopidine reduces eIF2α-phosphorylation, a measure of ER stress with a bell-shaped dose response curve. HEK293 cells were transfected with myc-Htt96Q (diamond) or myc-Htt20Q (square), then treated with increasing concentrations of pridopidine (from 0.03 to 150 µM equivalent to 0.01 µg/ml to 50 µg/ml) for 24 hours. The ratio of eIF2a-P to total eIF2a was quantified by immunoblot.
Figure 9:
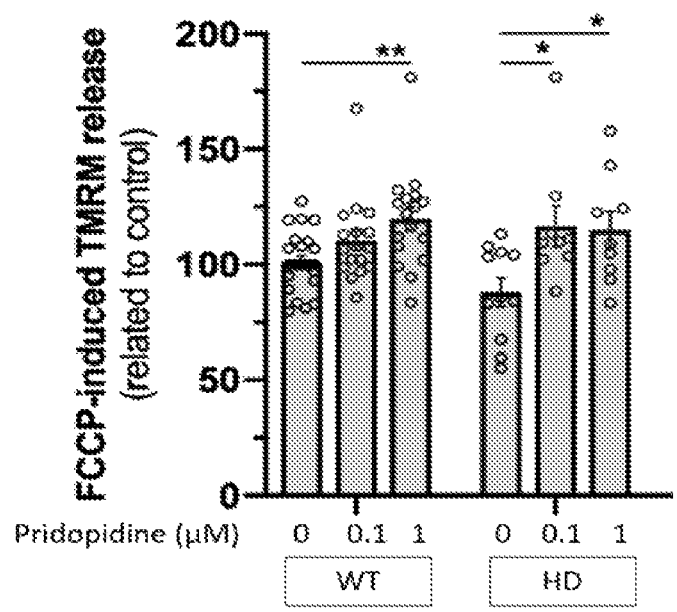
FIG. 9 Pridopidine increases mitochondrial membrane potential ($\Delta\Psi m$) in cortical HD neurons after oxidative stress. Striatal WT and YAC128 neurons expressing mutant huntingtin were treated with pridopidine for 24 h and TMRM was used to evaluate changes in $\Delta\Psi m$ after depolarization with oligomycin plus FCCP (n=7-10). 2-way ANOVA analysis revealed an effect of pridopidine treatment in striatal neurons [$F(2,107)=3.257$; $p=0.0423$].

The effects of pridopidine on ER stress were further studied by assessing phosphorylation levels of the translation initiation factor eIF2α. Phosphorylation of eIF2α is a hallmark of the ER stress response. STHdhQ7/7 cells expressing Htt96Q-mCherry show 3.5-fold increase in eIF2α-phosphorylation (eIF2α-p). Pridopidine a significant reduction in eIF2α-P (ratio of eIF2α-P/eIF2α) indicating a reduction in cellular ER stress, but the higher concentration does not (FIG. 8). The effective concentrations of 0.03-3 μM correlate to the human dose of 45 mg BID and below (Cmax ~2 μM).

Example 8: Mitochondrial Dysfunction

Mitochondrial Function is Impaired in Mutant GBA Neurons

Mitochondrial function was assessed in mutant GBA and WT neurons by measuring mitochondrial membrane potential (MMP, ΔΨm) using MitoTracker Red (MitoRed). Total mitochondrial content was determined using MitoTracker Green (MitoGreen). Compared to WT controls, mutant GBA neurons showed a lower baseline MMP but increased total mitochondrial content. The ratio of MitoRed to MitoGreen was significantly lower in mutant GBA neurons than in controls, supporting impaired mitochondrial function (Li et al. 2019).

Mitochondrial ROS levels were also assessed in live mutant GBA neurons using MitoSOX Red, a mitochondrial indicator of ROS. Compared to controls, mutant GBA neurons displayed increased MitoSOX Red fluorescence, indicating higher levels of superoxide production (Li et al. 2019).

Mitochondrial transport is additionally impaired as a result of GBA deficiency, likely as a result of increased levels of alpha-synuclein protein and its aggregation. Mitochondria movement was analyzed in hippocampal neurons into which exogenous wild-type (WT) or mutant (A35T) α-synuclein was genetically introduced. Over-expression of WT or A53T a-synuclein significantly reduces the average speed of mitochondria along the neurites of neurons (Xie and Chung 2012).

Clearance of aberrant or non-functional mitochondria, also known as mitophagy, is disrupted as a result of GBA deficiency. Mitophagy was induced in mutant GBA neurons by CCCP (Carbonyl cyanide m-chlorophenyl hydrazine, an uncoupler of mitochondrial oxidative phosphorylation) and assessed by measuring colocalization of MitoGreen-labelled mitochondria with LysoTracker Red-labelled lysosomes.

Mutant GBA neurons show less colocalization of mitochondria and lysosomes compared to WT, indicating impaired mitophagy (Li et al. 2019).

Pridopidine Reduces Mitochondrial ROS Production

Figure 10:
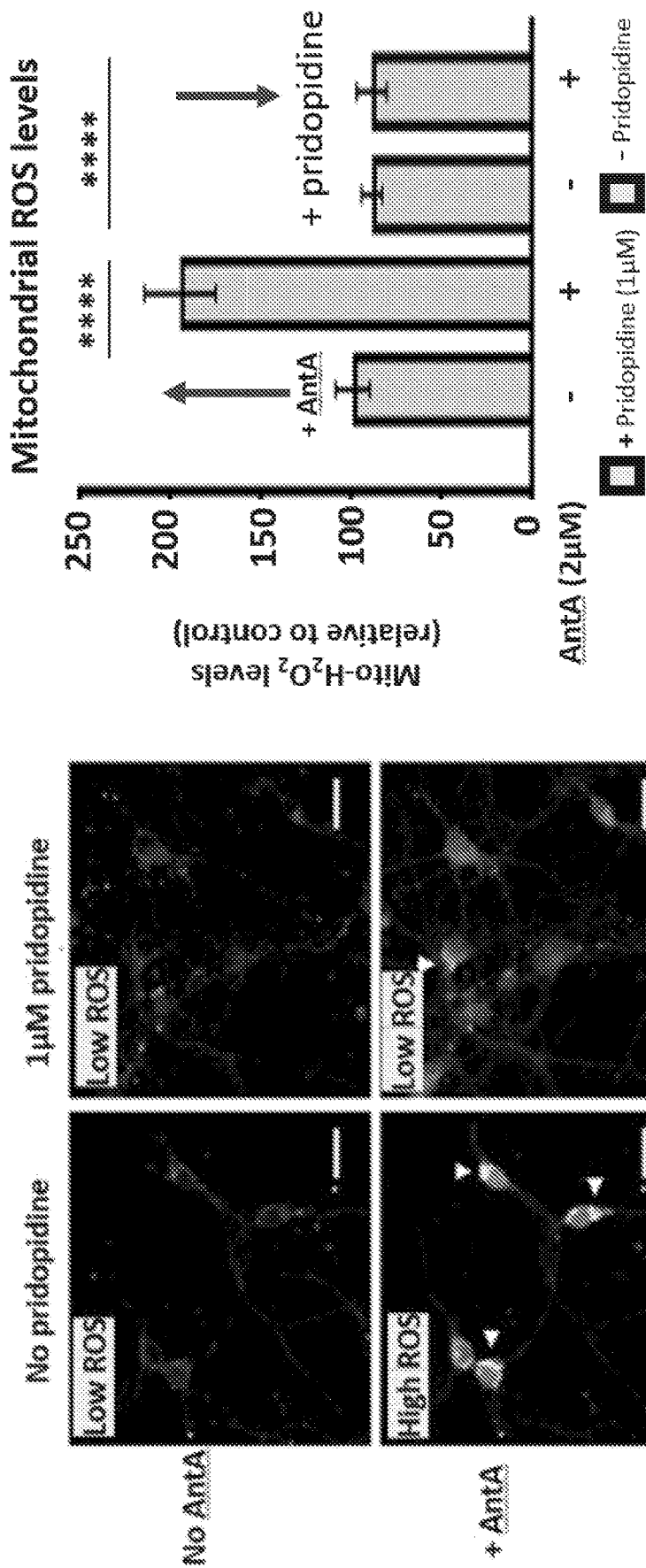
FIG. 10 Pridopidine Reduces Reactive Oxidative Species (ROS) in YAC128 HD striatal neurons. Striatal neurons treated or not with 1 µM pridopidine were incubated with MitoPY1 fluorescence probe. Mitochondrial $H_2O_2$ was recorded in spinning disk confocal before and after Antimycin A (Ant A, 2 µM), as indicated (n=4, considering ~20 cells/condition). Scale bar=30 µM. Two-way ANOVA reveals a rescuing effect of pridopidine treatment on mitochondrial ROS production [$F(1,389)=15.24$; $p<0.0001$].

HD mouse neurons show increased susceptibility to oxidative challenges, resulting in increased levels of ROS and a deficient antioxidant response. Striatal neurons from YAC128 HD mice were treated with 1 µM pridopidine (correlating to human exposure at <=45 mg BID) prior to induction of ROS production. Pridopidine shows robust and significant reduction of ROS production by mitochondria (FIG. 10).

Figure 11:
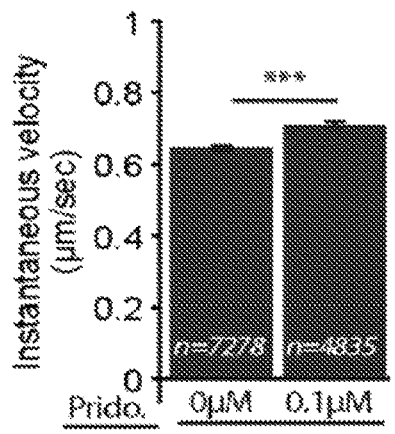
FIG. 11 Pridopidine increases mitochondrial velocity. Quantitative analysis of the velocity of mitochondria in axons reveals accelerated axonal transport mitochondria in WT neurons (n=number of particle steps) after application of 0.1 µM pridopidine (modified from Ionescu et al., 2019, FIG. 4F).

Pridopidine increases mitochondrial velocity. Mitochondrial transport was assessed in axons of wild-type motor neurons with or without locally applied pridopidine treatment, revealing that pridopidine accelerates mitochondria transport in axons. Effective concentration of 0.1 µM correlates to exposure at human dose <45 mg bid (Ionescu et al. 2019)(FIG. 11).

The genetic deletion of S1R leads to impaired mitophagy. During mitophagy process in wild-type (WT) retinal explants, both mitochondrial proteins VDAC1 and TIMM23 are substantially reduced in similar proportions. However, in S1R-/- retinal explants these two markers do not decrease, but rather increase 2-3 fold after induction of mitophagy, indicating impaired mitochondria clearance in S1R-/- cells compared to WT (Yang et al. 2019). Thus, S1R activity which is positively modulated by pridopidine is essential for mitophagy.

Example 9: Autophagic Defects

In SH-SY5Y cells in which GBA was genetically deleted by siRNA autophagy flux is reduced. Autophagy flux is measured by LC3B-II levels. High levels compared to the control indicate that the clearance of autophagosomes is impaired in GBA deficient cells (Magalhaes et al. 2016).

Reduced Autophagy Leads to α-Synuclein Aggregation in Primary Rat Cortical Neurons Accumulation and aggregation of the synaptic protein α-synuclein has a key role in PD pathogenesis. A significant increase in α-synuclein levels in the insoluble fraction, indicating its accumulation in aggregates was observed in rat cortical cells in which autophagy was reduced by application of phospholipase D inhibitor. Alpha-synuclein aggregation is a hallmark of PD and PD-GBA, and directly associated with neuronal cell death (Bae et al. 2014).

Activation of the S1R Enhances Autophagic Activity

HeLa cells treated with a S1R agonist were assessed for autophagic flux. Activation of the S1R significantly induces autophagic flux when compared to control conditions (Christ et al. 2019).

Example 10: BDNF

Plasma BDNF Levels are Reduced in Gaucher Disease (GD, GBA Mutation)

Brain-derived neurotrophic factor (BDNF) is important for development and survival of the nervous system, and key for synaptic plasticity. A reduction in BDNF levels is associated with neurodegenerative diseases such as PD and AD. In GD patients, BDNF levels in plasma are also greatly reduced. (Vairo et al. 2015).

Figure 12:
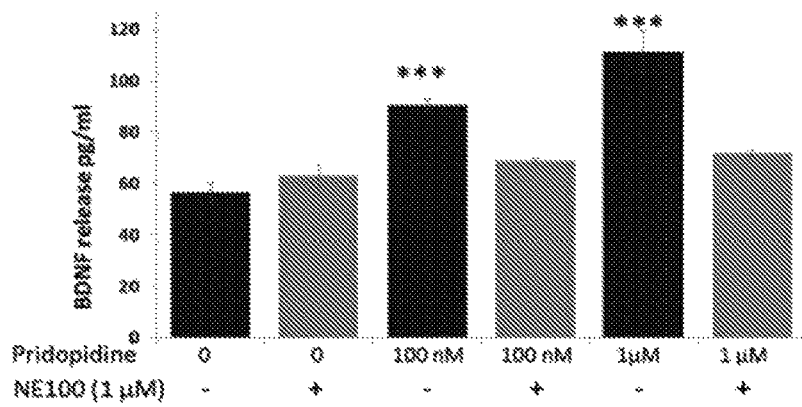
FIG. 12 Pridopidine enhances BDNF secretion in B104 neuroblastoma cell line. Data is expressed in pg/ml (mean 6 SEM; *P<0.05; P<0.01; *P<0.001; one-way ANOVA followed by Dunnett's test). NE100, sigma-1 receptor antagonist (1 µM). Source: Geva et al., 2016.

Pridopidine Enhances BDNF Secretion and Axonal Transport in a S1R-Mediated Mechanism Pridopidine at 100 nM and at 1 µM enhanced BDNF secretion in the B104 neuroblastoma cell line as compared to control untreated cells. BDNF secretion was inhibited when the cells were co-incubated with NE100, a known S1R antagonist (Geva et al. 2016)(FIG. 12). Effective concentration of 1 µM correlates to human dose <=45 mg bid.

Figure 13:
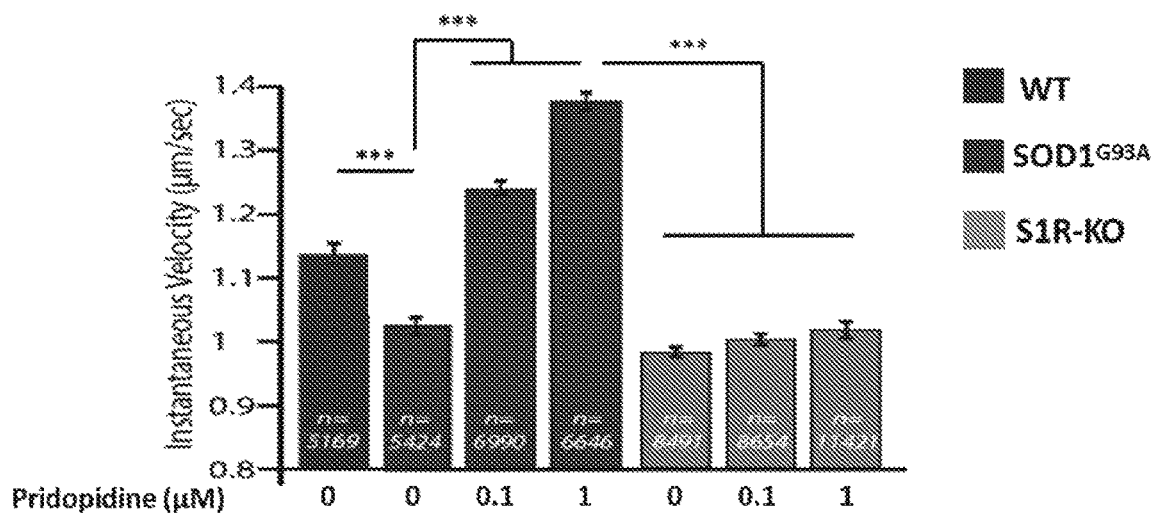
FIG. 13 Pridopidine enhances BDNF axonal transport in ALS motor neurons in a S1R-mediated mechanism. In order to visualize and analyze axonal transport, spinal cord extracts were plated in the proximal compartment of microfluidic chambers, and axons were allowed to grow through grooves to the distal compartment. Qdot-BDNF particles were introduced only into the distal chamber, and their retrograde transport through the axon visualized with a confocal spinning disk microscope. Bar chart of the Instantaneous Velocity values for Qdot-BDNF particles in WT ($1^{st}$ column from the left) or SOD1G93A ($2^{nd}$ to $4^{th}$ columns from the left) MNs show slower velocities in the SOD1G93A MNs. Pridopidine application accelerates the instantaneous velocities both SOD1G93A MNs (0.1 µM and 1 µM). S1R−/−MNs ($5^{th}$ to $7^{th}$ columns from the left) reveal defects in the axonal transport of BDNF. Pridopidine at either 0.1 µM or 1 µM was unable to recover these defects (n=number of qDot-BDNF steps). Data are shown as the mean±SEM. *p value<0.05; p value<0.01; *p value<0.001 (n=6 independent experiments; the sample size for each experiment is indicated on bars; Student's t test) (modified from Ionescu et al., 2019, FIG. 3C).

Pridopidine Treatment Rescues BDNF Axonal Transport in ALS Neurons in a S1R-Mediated Mechanism BDNF axonal transport velocity is significantly reduced in ALS SOD1G93A motor neurons. Treatment of cultures with 0.1 and 1 µM pridopidine significantly accelerates the velocity in SOD1G93A motor neurons in a dose-dependent manner. 1 µM pridopidine correlates to human dose <=45 mg bid. This effect is abolished in motor neurons in which S1R has been genetically deleted, pointing to a S1R-dependent mechanism (Ionescu et al. 2019)(FIG. 13).

What is claimed is:

1. A method for treating, or slowing the progression of Parkinson's Disease in a subject wherein the Parkinson's Disease is associated with a glucocerebrosidase mutation (PD-GBA) wherein the method comprises administering a pharmaceutical composition comprising pridopidine or pharmaceutically acceptable salt thereof to the subject, wherein the pridopidine or pharmaceutically acceptable salt thereof is administered in a dosage of between 1 to 100 mg per day.

2. The method of claim 1, comprising treating, slowing, or reversing neurodegeneration in the subject.

3. The method of claim 2, wherein the neurodegeneration in the subject is presented as increased ER stress, neuronal mitochondrial dysfunction, decreased autophagic flux, decreased plasma BDNF levels, decreased cerebrospinal fluid (CSF) BDNF levels or decreased neuronal and BDNF axonal transport.

4. The method of claim 1, comprising administering to the subject a pharmaceutical composition comprising pridopidine or pharmaceutically acceptable salt thereof at least twice a day.

5. The method of claim 4, comprising administering to the subject a pharmaceutical composition comprising pridopidine or pharmaceutically acceptable salt thereof twice a day.

6. The method of claim 4, comprising administering to the subject a pharmaceutical composition comprising pridopidine or pharmaceutically acceptable salt thereof three times a day.

7. The method of claim 4, comprising administering to the subject a pharmaceutical composition comprising pridopidine or pharmaceutically acceptable salt thereof four times a day.

8. The method of claim 1, wherein the total administered dosage of the pridopidine or pharmaceutically acceptable salt thereof is 10 to 100 mg per day.

9. The method of claim 8, wherein the total administered dosage of the pridopidine or pharmaceutically acceptable salt thereof is 50 to 100 mg per day.

10. The method of claim 9, wherein the total administered dosage of the pridopidine or pharmaceutically acceptable salt thereof is 80 to 100 mg per day.

11. The method of claim 10, wherein the total administered dosage of the pridopidine or pharmaceutically acceptable salt thereof is 80 mg per day.

12. The method of claim 10, wherein the total administered dosage of the pridopidine or pharmaceutically acceptable salt thereof is 90 mg per day.

13. The method of claim 10, wherein the total administered dosage of the pridopidine or pharmaceutically acceptable salt thereof is 100 mg per day.

14. The method of claim 1, comprising administering to the subject a pharmaceutical composition comprising pridopidine or pharmaceutically acceptable salt thereof twice a day, wherein the total administered dosage of the pridopidine or pharmaceutically acceptable salt thereof is 80 to 100 mg per day.

15. The method of claim 14, comprising administering to the subject a pharmaceutical composition comprising pridopidine or pharmaceutically acceptable salt thereof twice a day, wherein the total administered dosage of the pridopidine or pharmaceutically acceptable salt thereof is 90 mg per day.

16. The method of claim 15, comprising administering to the subject a pharmaceutical composition comprising pridopidine or pharmaceutically acceptable salt thereof twice a day, wherein each one of the two pharmaceutical composition comprises a different dosage of pridopidine or pharmaceutically acceptable salt thereof, wherein the total administered dosage of the pridopidine or pharmaceutically acceptable salt thereof is 90 mg per day.

17. The method of claim 15, comprising administering to the subject a pharmaceutical composition comprising 45 mg pridopidine or pharmaceutically acceptable salt thereof twice a day, wherein the total administered dosage of the pridopidine or pharmaceutically acceptable salt thereof is 90 mg per day.

18. The method of claim 1, comprising systemically administering the pharmaceutical composition comprising pridopidine or pharmaceutically acceptable salt thereof to the subject.

19. The method of claim 18, comprising orally administering the pharmaceutical composition comprising pridopidine or pharmaceutically acceptable salt thereof to the subject.

20. The method of claim 18, wherein the pharmaceutical composition comprising pridopidine or pharmaceutically acceptable salt thereof is administered in a form selected from the group consisting of an inhalable powder, an injectable, a liquid, a gel, a solid, a capsule or a tablet.

21. The method of claim 1, wherein the pharmaceutically acceptable pridopidine salt is pridopidine hydrochloride.

* * * * *